United States Patent
Hashino et al.

(10) Patent No.: US 9,339,423 B2
(45) Date of Patent: May 17, 2016

(54) ABSORBENT ARTICLE

(71) Applicant: UNICHARM CORPORATION, Shikokuchuo-shi, Ehime (JP)

(72) Inventors: Akira Hashino, Kanonji (JP); Yuki Noda, Kanonji (JP); Tatsuya Tamura, Kanonji (JP); Takashi Nomoto, Kanonji (JP); Takashi Onozuka, Kanonji (JP); Tomoyuki Saga, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 14/389,999

(22) PCT Filed: Mar. 26, 2013

(86) PCT No.: PCT/JP2013/058836
§ 371 (c)(1),
(2) Date: Oct. 1, 2014

(87) PCT Pub. No.: WO2013/150921
PCT Pub. Date: Oct. 10, 2013

(65) Prior Publication Data
US 2015/0080838 A1    Mar. 19, 2015

(30) Foreign Application Priority Data
Apr. 2, 2012  (JP) ................ 2012-083814

(51) Int. Cl.
*A61F 13/15*  (2006.01)
*A61F 13/512*  (2006.01)
(Continued)

(52) U.S. Cl.
CPC .......... *A61F 13/512* (2013.01); *A61F 13/5123* (2013.01); *A61F 13/51113* (2013.01);
(Continued)

(58) Field of Classification Search
CPC .............. A61F 13/512; A61F 13/5123; A61F 2013/5127; A61F 2013/53782; A61F 13/51113
See application file for complete search history.

(56) References Cited

U.S. PATENT DOCUMENTS

| 3,929,135 A | 12/1975 | Thompson |
| 4,588,630 A | 5/1986 | Shimalla |

(Continued)

FOREIGN PATENT DOCUMENTS

| CN | 1432352 A | 7/2003 |
| EP | 0545423 A1 | 6/1993 |

(Continued)

OTHER PUBLICATIONS

International Search Report mailed Jul. 3, 2012 in corresponding International Application No. PCT/JP2012/058499.
(Continued)

*Primary Examiner* — Susan Su
(74) *Attorney, Agent, or Firm* — Hauptman Ham, LLP

(57) ABSTRACT

An absorbent article is provided to prevent pulp fibers and a superabsorbent polymer that constitute an absorbent body from leaking from openings, even if a top sheet does not cover the side wall portions of the absorbent body at the openings. The absorbent article includes: a liquid-permeable top sheet having openings; a back sheet; and an absorbent body having openings. At the openings of the top sheet and the openings of the absorbent body, the top sheet is detached from the absorbent body. The opening diameters of the openings on the clothing side of the top sheet are smaller than the opening diameters of the openings on the skin side of the absorbent body. An opening diameter of the openings on the clothing side of the absorbent body is no greater than the opening diameter of the openings on the clothing side of the top sheet.

11 Claims, 7 Drawing Sheets

(51) Int. Cl.
*A61F 13/511* (2006.01)
*A61F 13/534* (2006.01)
*A61L 15/60* (2006.01)
*A61L 15/20* (2006.01)
*A61F 13/537* (2006.01)
*A61L 15/50* (2006.01)

(52) U.S. Cl.
CPC .............. *A61F13/534* (2013.01); *A61L 15/20* (2013.01); *A61L 15/60* (2013.01); *A61F 2013/5127* (2013.01); *A61F 2013/53782* (2013.01); *A61L 15/50* (2013.01)

(56) References Cited

U.S. PATENT DOCUMENTS

| | | | |
|---|---|---|---|
| 4,759,754 A | 7/1988 | Korpman | |
| 5,078,710 A | 1/1992 | Suda et al. | |
| 5,334,176 A | 8/1994 | Buenger et al. | |
| 5,344,416 A | 9/1994 | Niihara | |
| 5,387,209 A * | 2/1995 | Yamamoto | A61F 13/512 604/358 |
| 5,614,283 A | 3/1997 | Potnis et al. | |
| 5,650,214 A | 7/1997 | Anderson et al. | |
| 6,153,209 A | 11/2000 | Vega et al. | |
| 6,730,819 B1 | 5/2004 | Pesce | |
| 2001/0029141 A1 | 10/2001 | Mizutani et al. | |
| 2003/0088222 A1 | 5/2003 | Yoshimasa et al. | |
| 2003/0149410 A1 | 8/2003 | Kudo et al. | |
| 2003/0198784 A1 | 10/2003 | Mizutani et al. | |
| 2004/0039363 A1 * | 2/2004 | Sugiyama | A61F 13/49473 604/385.101 |
| 2005/0148971 A1 | 7/2005 | Kuroda et al. | |
| 2006/0184150 A1 | 8/2006 | Noel | |
| 2006/0276767 A1 | 12/2006 | Ueminami et al. | |
| 2007/0073256 A1 * | 3/2007 | Ponomarenko | A61F 13/495 604/385.13 |
| 2007/0219515 A1 | 9/2007 | Marsh et al. | |
| 2007/0298213 A1 | 12/2007 | Noda et al. | |
| 2007/0298214 A1 | 12/2007 | Noda et al. | |
| 2007/0298220 A1 | 12/2007 | Noda et al. | |
| 2007/0298667 A1 | 12/2007 | Noda et al. | |
| 2007/0298671 A1 | 12/2007 | Noda et al. | |
| 2007/0299416 A1 | 12/2007 | Noda et al. | |
| 2008/0010795 A1 | 1/2008 | Mizutani et al. | |
| 2008/0044622 A1 | 2/2008 | Noda et al. | |
| 2008/0044628 A1 | 2/2008 | Noda et al. | |
| 2008/0045915 A1 | 2/2008 | Noda et al. | |
| 2008/0085399 A1 | 4/2008 | Noda et al. | |
| 2008/0132136 A1 | 6/2008 | Uematsu et al. | |
| 2008/0200894 A1 | 8/2008 | Gatto et al. | |
| 2009/0221978 A1 | 9/2009 | Gatto et al. | |
| 2009/0282660 A1 | 11/2009 | Noda et al. | |
| 2009/0299316 A1 * | 12/2009 | Seyler | A61F 13/53713 604/378 |
| 2010/0069874 A1 | 3/2010 | Noda et al. | |
| 2010/0137824 A1 | 6/2010 | Uematsu et al. | |
| 2010/0191207 A1 | 7/2010 | Oba et al. | |
| 2011/0004176 A1 * | 1/2011 | Andersson | A61F 13/512 604/378 |
| 2011/0060303 A1 * | 3/2011 | Bissah | A61F 13/4756 604/372 |
| 2011/0319851 A1 | 12/2011 | Kudo et al. | |
| 2012/0004633 A1 * | 1/2012 | R. Marcelo | A61F 13/4756 604/378 |
| 2012/0045620 A1 | 2/2012 | Oba et al. | |
| 2012/0141742 A1 | 6/2012 | Yamaguchi et al. | |
| 2012/0177889 A1 | 7/2012 | Uematsu et al. | |
| 2012/0196091 A1 | 8/2012 | Mizutani et al. | |
| 2012/0220971 A1 * | 8/2012 | Harada | A61F 13/4704 604/380 |
| 2012/0220972 A1 * | 8/2012 | Kawamura | A61F 13/535 604/383 |
| 2012/0277711 A1 * | 11/2012 | Kim | A61F 13/4756 604/374 |
| 2013/0034686 A1 | 2/2013 | Mitsuno | |
| 2013/0137328 A1 | 5/2013 | Mitsuno | |
| 2013/0211360 A1 * | 8/2013 | Hashino | A61F 13/15699 604/380 |
| 2013/0226123 A1 | 8/2013 | Kudo et al. | |
| 2014/0163508 A1 * | 6/2014 | Tanaka | A61F 13/51405 604/382 |
| 2014/0336608 A1 * | 11/2014 | Hao | B32B 3/30 604/385.01 |

FOREIGN PATENT DOCUMENTS

| | | |
|---|---|---|
| EP | 1166732 A2 | 1/2002 |
| EP | 1201213 A2 | 5/2002 |
| EP | 1250940 A1 | 10/2002 |
| EP | 1290995 A2 | 3/2003 |
| EP | 1362568 A2 | 11/2003 |
| EP | 1371379 A1 | 12/2003 |
| EP | 2036521 A1 | 3/2009 |
| EP | 2433602 A1 | 3/2012 |
| GB | 2262235 | 6/1993 |
| JP | S57-17081 | 4/1982 |
| JP | S64-34365 | 2/1989 |
| JP | S64-56051 | 3/1989 |
| JP | H01-158954 | 6/1989 |
| JP | 02152920 A | 6/1990 |
| JP | H02-229255 | 9/1990 |
| JP | H05-154176 | 6/1993 |
| JP | H06-5614 U | 1/1994 |
| JP | 6502104 A | 3/1994 |
| JP | H07-84697 | 9/1995 |
| JP | H08-510665 | 11/1996 |
| JP | H08-322879 | 12/1996 |
| JP | H10-95810 | 4/1998 |
| JP | H10-510743 A | 10/1998 |
| JP | H11-512643 | 11/1999 |
| JP | 2000-510376 | 8/2000 |
| JP | 3091283 | 9/2000 |
| JP | 2000-512886 A | 10/2000 |
| JP | 2001-095845 | 4/2001 |
| JP | 2001-129019 | 5/2001 |
| JP | 2001-328191 | 11/2001 |
| JP | 2002-508693 | 3/2002 |
| JP | 3262172 | 3/2002 |
| JP | 2002528174 A | 9/2002 |
| JP | 2002537904 A | 11/2002 |
| JP | 200324372 A | 1/2003 |
| JP | 200352750 A | 2/2003 |
| JP | 2004-500908 | 1/2004 |
| JP | 200449529 A | 2/2004 |
| JP | 2005-504591 A | 2/2005 |
| JP | 2005-095759 | 4/2005 |
| JP | 2005193001 A | 7/2005 |
| JP | 2005-525134 A | 8/2005 |
| JP | 2006501022 A | 1/2006 |
| JP | 2006-510456 | 3/2006 |
| JP | 2006115996 A | 5/2006 |
| JP | 2006-255051 | 9/2006 |
| JP | 2006280526 A | 10/2006 |
| JP | 200714705 A | 1/2007 |
| JP | 2007-509695 A | 4/2007 |
| JP | 2008-002034 A | 1/2008 |
| JP | 2008-023311 A | 2/2008 |
| JP | 2008-025080 | 2/2008 |
| JP | 2008-025081 | 2/2008 |
| JP | 2008-025082 | 2/2008 |
| JP | 2008-025083 | 2/2008 |
| JP | 2008-025084 A | 2/2008 |
| JP | 2008-025085 A | 2/2008 |
| JP | 2008-503323 A | 2/2008 |
| JP | 200823365 A | 2/2008 |
| JP | 200825078 A | 2/2008 |
| JP | 200825079 A | 2/2008 |
| JP | 200829830 A | 2/2008 |
| JP | 2008-138340 A | 6/2008 |
| JP | 2008-144322 A | 6/2008 |
| JP | 2008-529721 A | 8/2008 |
| JP | 2008229032 A | 10/2008 |
| JP | 2008229033 A | 10/2008 |

(56) References Cited

FOREIGN PATENT DOCUMENTS

| | | |
|---|---|---|
| JP | 2008237569 A | 10/2008 |
| JP | 2008-264084 A | 11/2008 |
| JP | 2008-266813 A | 11/2008 |
| JP | 2008-541943 A | 11/2008 |
| JP | 2008-307179 | 12/2008 |
| JP | 20095767 A | 1/2009 |
| JP | 2009-030218 A | 2/2009 |
| JP | 2009-201878 | 9/2009 |
| JP | 2009297048 A | 12/2009 |
| JP | 201088822 A | 4/2010 |
| JP | 2010-518918 A | 6/2010 |
| JP | 2010518918 A | 6/2010 |
| JP | 2010-148708 A | 7/2010 |
| JP | 2010526629 A | 8/2010 |
| JP | 2010-285735 | 12/2010 |
| JP | 2010279568 A | 12/2010 |
| JP | 2011-038211 | 2/2011 |
| JP | 2011-074515 A | 4/2011 |
| JP | 2011-080178 | 4/2011 |
| JP | 201167484 A | 4/2011 |
| JP | 201172650 A | 4/2011 |
| JP | 2011510801 A | 4/2011 |
| JP | 4693847 B2 | 6/2011 |
| JP | 2011104001 A | 6/2011 |
| JP | 2011104059 A | 6/2011 |
| JP | 2011120696 A | 6/2011 |
| JP | 2011226010 A | 11/2011 |
| JP | 2011226011 A | 11/2011 |
| JP | 2012-50626 A | 3/2012 |
| JP | 5122007 B1 | 1/2013 |
| WO | 9301781 A1 | 2/1993 |
| WO | 94/27539 | 12/1994 |
| WO | 96/19173 A1 | 6/1996 |
| WO | 98/55158 A2 | 12/1998 |
| WO | 99/00093 | 1/1999 |
| WO | 99/25288 A1 | 5/1999 |
| WO | 99/29274 | 6/1999 |
| WO | 0024351 A1 | 5/2000 |
| WO | 01/45757 | 6/2001 |
| WO | 03/017900 A1 | 3/2003 |
| WO | 03/028776 A1 | 4/2003 |
| WO | 2004030713 A1 | 4/2004 |
| WO | 2004/058119 | 7/2004 |
| WO | 2005/044164 A1 | 5/2005 |
| WO | 2006/009996 A1 | 1/2006 |
| WO | 2006/130646 A1 | 12/2006 |
| WO | 2007/034451 A1 | 3/2007 |
| WO | 2008072675 A1 | 6/2008 |
| WO | 2008101163 A2 | 8/2008 |
| WO | 2008139425 A1 | 11/2008 |
| WO | 2008/149771 | 12/2008 |
| WO | 2009102837 A2 | 8/2009 |
| WO | 2012/133724 A1 | 10/2012 |

OTHER PUBLICATIONS

International Search Report mailed Mar. 19, 2013 in corresponding International Application No. PCT/JP2012/082087.
International Search Report mailed Mar. 12, 2013 in corresponding International Application No. PCT/JP2012/082104.
International Search Report mailed Mar. 19, 2013 in corresponding International Application No. PCT/JP2013/054382.
International Search Report mailed May 21, 2014 in corresponding International Application No. PCT/JP2013/054796.
International Search Report mailed Mar. 26, 2013, corresponds to International Application No. PCT/JP2012/082977.
International Search Report mailed Jan. 8, 2013, corresponds to International Application No. PCT/JP2012/075583.
International Search Report mailed Jul. 17, 2012, corresponds to International Application No. PCT/JP2012/061505.
Corresponding International Application No. PCT/JP2012/058499 Written Opinion dated Jul. 3, 2012.
Corresponding International Application No. PCT/JP2012/058499 Reply to Written Opinion dated Jan. 30, 2013.
International Search Report mailed May 21, 2013, corresponds to International Application No. PCT/JP2013/058859.
International Search Report mailed Jun. 18, 2013, corresponds to International Application No. PCT/JP2013/058855.
Atsushi Fujita, "Prediction of Organic Compounds and Organic Conceptual Diagram", Kagaku no Ryoiki (Region of Chemistry), Oct. 1957, p. 719-725, vol. 11, No. 10.
International Search Report mailed Jul. 2, 2013, corresponds to International Application No. PCT/JP2013/058860.
International Search Report mailed Jul. 2, 2013, corresponds to International Application No. PCT/JP2013/058862.
International Search Report mailed Jul. 2, 2013, corresponds to International Application No. PCT/JP2013/058861.
International Search Report mailed May 14, 2013, corresponds to International Application No. PCT/JP2013/058836.

* cited by examiner (a)

(b)

200 μm (a)

50 μm (b)

50 μm (a)

(b)

ABSORBENT ARTICLE

CROSS-REFERENCES TO RELATED APPLICATIONS

The present application is a National Phase of International Application Number PCT/JP2013/058836 filed Mar. 26, 2013, which claims the priority of Japanese patent Application No. 2012-083814 filed Apr. 2, 2012.

TECHNICAL FIELD

The present invention relates to an absorbent article, such as a sanitary napkin, panty liner, incontinence pad or incontinence liner.

BACKGROUND ART

Absorbent articles having dot-like compressed sections formed by heat embossing treatment, in which the front side material alone is compressed, are known in the prior art (PTL 1, for example). In the dot-like compressed sections of the absorbent article, the nonwoven fabric of the front side material is formed as a film. The surface material film covers the side walls of the hole interiors, preventing the pulp fibers or super-absorbent polymer (SAP) composing the absorbent body from escaping from the dot-like compressed sections.

CITATION LIST

Patent Literature

[PTL 1] Japanese Patent Publication No. 4693847

SUMMARY OF THE INVENTION

Technical Problem

In the absorbent article described in PTL 1, however, the nonwoven fabric of the surface material is formed as a film, and the surface material film is compressed until it covers the side walls in the holes, such that the fiber density of the absorbent body is often increased around the openings formed by heat embossing treatment. In such cases, body fluid absorbed by the absorbent body collects around the openings, and body fluid absorbed by the absorbent body sometimes leaks through the openings. Also, the fiber density of the absorbent body as a whole is increased, often weakening the absorption property of the absorbent body.

It is an object of the present invention to provide an absorbent article that can inhibit the pulp fiber or super-absorbent polymer (SAP) composing the absorbent body from escaping from the openings even if the top sheet does not cover the side walls of the absorbent body at the openings.

Solution to Problem

In order to solve the aforementioned problems, the invention employs the following construction.

Specifically, the invention is an absorbent article comprising a liquid-permeable top sheet provided on the skin side and having openings running through in the thickness direction, a liquid-impermeable back sheet provided on the clothing side, and a liquid-retaining absorbent body situated between the top sheet and the back sheet and having openings that are provided at a location in the thickness direction corresponding to the openings of the top sheet and that run through the thickness direction, or else extend in but do not run through the thickness direction, wherein the top sheet is detached from the absorbent body at the openings of the top sheet and the openings of the absorbent body, and the opening diameters of the openings on the clothing side of the top sheet are smaller than the opening diameters of the openings on the skin side of the absorbent body.

Another aspect of the invention is an absorbent article comprising a liquid-permeable top sheet provided on the skin side and having openings running through in the thickness direction, a liquid-impermeable back sheet provided on the clothing side, a liquid-retaining absorbent body situated between the top sheet and the back sheet and having openings that are provided at a location in the thickness direction corresponding to the openings of the top sheet and that run through the thickness direction, or else extend in but do not run through the thickness direction, and a liquid-permeable second sheet provided between the top sheet and the absorbent body, and having openings that are provided at locations in the thickness direction corresponding to the openings of the top sheet and that run through the thickness direction, wherein the second sheet is detached from the absorbent body at the openings of the second sheet and the openings of the absorbent body, and the opening diameters of the openings on the clothing side of the second sheet are smaller than the opening diameters of the openings on the skin side of the absorbent body.

Advantageous Effect of the Invention

According to the invention, it is possible to prevent the pulp fiber or super-absorbent polymer (SAP) composing the absorbent body from escaping from the openings even if the top sheet does not cover the side walls of the absorbent body at the openings.

DESCRIPTION OF EMBODIMENTS

Figure 1:
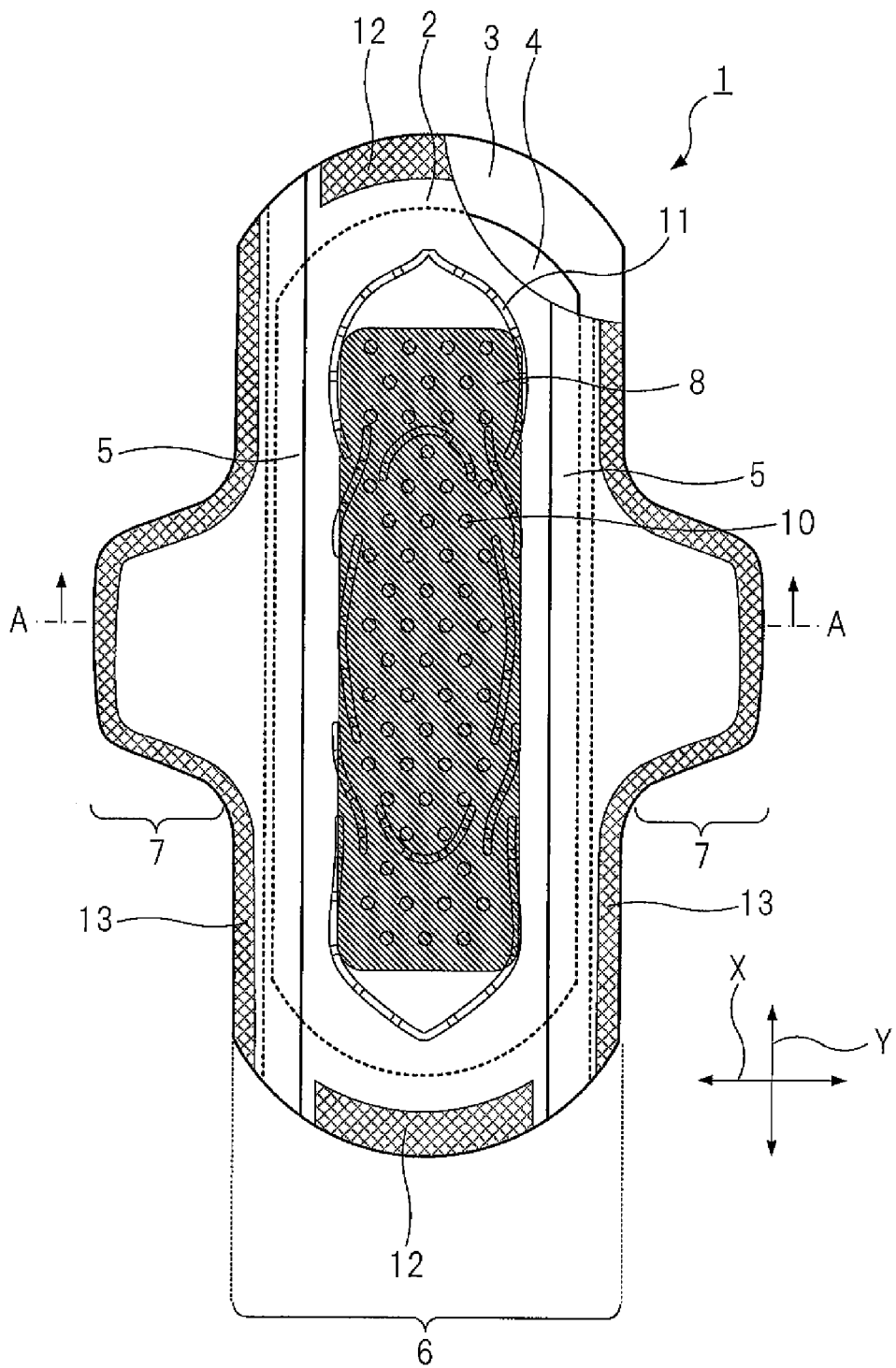
FIG. 1 is a partial cutaway plan view of an absorbent article according to an embodiment of the invention.

An absorbent article according to an embodiment of the invention will now be explained with reference to the accompanying drawings. However, the invention is not limited to the examples depicted in the drawings.

Figure 2:
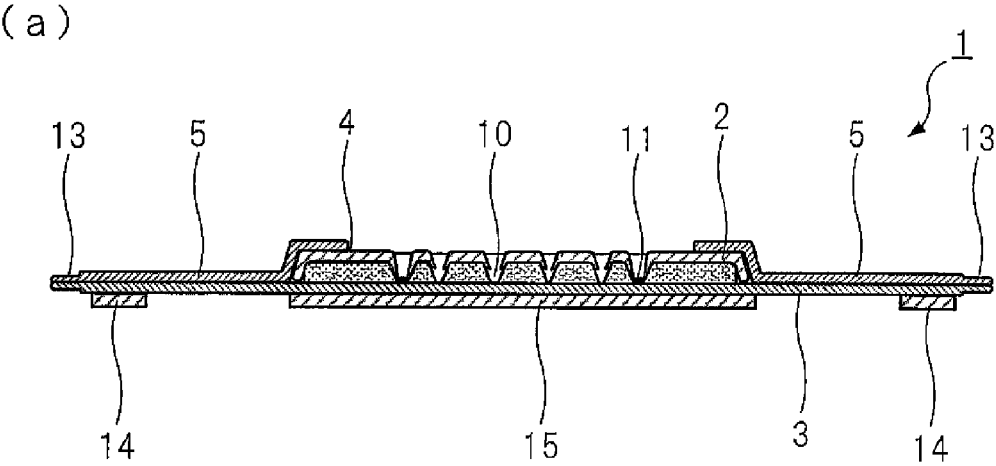
FIG. 2($a$) is a schematic cross-sectional view showing a cross-section of FIG. 1 along line A-A, and FIG. 2($b$) is a simplified cross-sectional view of an opening of an absorbent article according to an embodiment of the invention.
Figure 2:
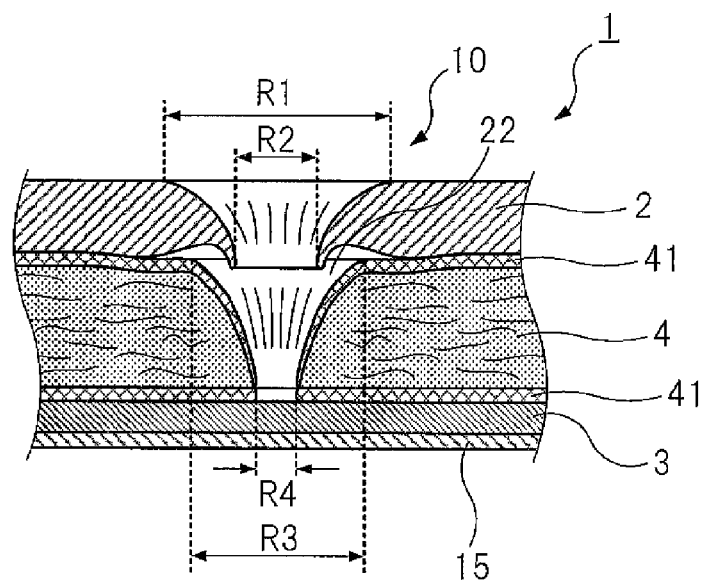

FIG. 1 is partial cutaway plan view showing an embodiment of an absorbent article of the invention, and FIG. 2 is a schematic cross-sectional view showing a cross-section of FIG. 1 along line A-A. The absorbent article 1 comprises a liquid-permeable top sheet 2 provided on the skin side, a liquid-impermeable back sheet 3 provided on the clothing side, and a liquid-retaining absorbent body 4 situated between the top sheet 2 and the back sheet 3. The absorbent article 1 also has openings 10 running through the top sheet 2 and the absorbent body 4 in the thickness direction.

Specifically, the openings 10 of the absorbent body 4 are provided at locations in the thickness direction corresponding to the openings 10 of the top sheet. The top sheet 2 has a blood modifying agent-coated region 8 coated with a blood modifying agent in at least a portion of the region in which the openings 10 are formed. The outer side of the absorbent body 4 is covered with a wrap sheet 41 (see FIG. 2(b)).

The absorbent article 1 further comprises a pair of side sheets 5 provided over both sides in the widthwise direction of the top sheet 2. The absorbent article 1 further has a body section 6 and a pair of wing sections 7 extending from the body section 6 in the widthwise direction. The wing sections 7 are each constructed from a side sheet 5 and a back sheet 3.

The top sheet 2 and absorbent body 4 have compressed grooves 11 from the top sheet 2 to the interior of the absorbent body 4, formed by compression in the thickness direction by embossing. The compressed grooves 11 help prevent body fluid that has been discharged into the absorbent article 1 from diffusing in the widthwise direction (X direction). This can inhibit peeling of the top sheet 2 from the absorbent body 4. The compressed grooves 11 surround the section of the absorbent article 1 that contacts the excretory opening of the wearer, and they have roughly annular discontinuous shapes.

The top sheet 2 and back sheet 3 are bonded at a seal section 12 by heat embossing. The back sheet 3 and side sheet 5 are also bonded at a seal section 13 by heat embossing. The seal sections 12,13 are provided on the outer periphery of the absorbent article 1. Pressure-sensitive adhesive sections 14,15 are provided on the clothing side of the back sheet 3. In FIG. 1, the widthwise direction of the absorbent article 1 is the X direction, and the lengthwise direction is the Y direction. The planar direction is the direction of the plane that extends in the XY direction.

The shape of the body section 6 is not particularly restricted so long as it is a shape suited to the female body and the shape of shorts, such as roughly rectangular, roughly elliptical or roughly hourglass-shaped. The dimensions of extension in the lengthwise direction of the outer shape of the body section 6 are preferably 100 to 500 mm and more preferably 150 to 350 mm. The dimensions of extension in the widthwise direction of the outer shape of the body section 6 are preferably 30 to 200 mm and more preferably 40 to 180 mm.

The top sheet 2 transfers body fluid that has been excreted from the wearer into the absorbent body 4 provided under it. The top sheet 2 holds the absorbent body 4 in a manner with the absorbent body 4 held between it and the back sheet 3. All or a portion of the top sheet 2 is liquid-permeable, and the liquid-permeable areas of the top sheet 2 may be formed of a liquid-permeable nonwoven fabric or woven fabric, a resin film with a plurality of liquid-permeable holes formed therein, or a net-like sheet with a plurality of mesh holes.

The material used for the nonwoven fabric or woven fabric in the top sheet 2 may be either natural fibers or chemical fibers. Examples of natural fibers include cellulose such as ground pulp and cotton. Examples of chemical fibers include regenerated cellulose such as rayon and fibril rayon, semi-synthetic cellulose such as acetate and triacetate, thermoplastic hydrophobic chemical fibers, and hydrophilicized thermoplastic hydrophobic chemical fibers. Thermoplastic hydrophobic chemical fibers include monofilaments of polyethylene (PE), polypropylene (PP) and polyethylene terephthalate (PET), fibers obtained by graft polymerization of PE and PP, and composite fibers with a core-sheath structure or the like.

Fabrication of a nonwoven fabric to be used in the top sheet 2 may be accomplished by web forming, with either a dry method (carding method, spunbond method, meltblown method or airlaid method) or wet method, or with a combination of a dry method and a wet method. The web bonding method for fabrication of a nonwoven fabric to be used in the top sheet 2 may be thermal bonding, needle punching, chemical bonding or the like, with no particular restriction to these methods. Spunlace formed into a sheet by a hydroentangling method may also be used in the top sheet 2. There may also be used for the top sheet 2 a nonwoven fabric having concavoconvexities on the skin side, such as a nonwoven fabric having heat-shrinkable fibers or the like for shrinking on the lower layer side to form concavoconvexities on the upper layer side, or a nonwoven fabric in which concavoconvexities are formed by applying air during web formation. Forming concavoconvexities on the skin side in this manner can reduce the contact area between the top sheet 2 and the skin.

As fibers in the nonwoven fabric for the top sheet 2 there may be used core-sheath type fibers wherein the melting point of the core component is higher than that of the sheath component, eccentric core-sheath type fibers, or side-by-side type composite fibers wherein the melting points of the left and right components differ. In addition, hollow type fibers or flat fibers, or irregularly shaped fibers such as Y-shaped fibers or C-shaped fibers, solid crimped fibers such as latent crimped or developed crimped fibers, or split fibers that have been split by a physical load such as a water stream, heat or embossing, may be combined in a nonwoven fabric to be used for the top sheet 2.

In consideration of uptake of fluids and feel on the skin, the size of the fibers of the nonwoven fabric used for the top sheet 2 is preferably 1.1-8.8 dtex.

When hydrophobic synthetic fibers are used in the top sheet 2, in consideration of uptake of fluids and rewet-back by the top sheet 2, the hydrophobic synthetic fibers may be mixed with a hydrophilic agent, water-repellent agent or the like, or the hydrophobic synthetic fibers may be coated with a hydrophilic agent, water-repellent agent or the like. The hydrophobic synthetic fibers may also be imparted with hydrophilicity by corona treatment or plasma treatment. This will result in sparsely dispersed hydrophilic areas and lipophilic areas in the blood modifying agent-coated region 8 when the blood modifying agent is lipophilic, and both the hydrophilic components (mainly plasma) and lipophilic components (mainly blood cells) in body fluid (such as menstrual blood) will rapidly migrate from the top sheet 2 into the absorbent body 4.

In order to increase the concealing property of the top sheet 2, an inorganic filler such as titanium oxide, barium sulfate or calcium carbonate may be added to the fibers of the nonwoven fabric used in the top sheet 2. When the nonwoven fabric fibers are core-sheath type composite fibers, the inorganic filler may be added only to the core or only to the sheath.

When a resin film or net-like sheet is to be used as the top sheet 2, the resin film or net-like sheet can be formed from polypropylene (PP), polyethylene (PE), polyethylene terephthalate (PET), or the like.

As mentioned above, the top sheet 2 has openings 10. If the opening diameter of each opening 10 on the skin side of the top sheet 2 (the opening diameter, or when the shapes of the openings in the planar direction (XY direction) are not circular, the diameter of a circumscribed circle of each opening is defined as the opening diameter), is represented by R1, and the opening diameter of each opening 10 on the clothing side of the top sheet 2 is represented by R2 (see FIG. 2(b)), the opening diameter R1 is preferably larger than the opening diameter R2. This will allow body fluid discharged into the top sheet 2 to collect, and will allow the body fluid to be transferred into the openings 10 of the absorbent body 4, as explained below. For example, the opening diameter R1 has a size of preferably 110% or greater and more preferably 130% or greater than the opening diameter R2. The opening diameter R1 is preferably 0.11 to 3.3 mm and more preferably 0.33 to 3 mm. The opening diameter R2 is preferably 0.1 to 3 mm and more preferably 0.3 to 2.7 mm.

At the openings 10, the top sheet 2 is detached from the absorbent body 4. Therefore, the structural material of the absorbent body 4, such as the hydrophilic fibers and super-absorbent polymer (SAP) that has escaped out through the openings 10 of the absorbent body 4, must pass through the small openings 10 on the clothing side of the top sheet 2 after it has moved into the wide spaces 22 in the widthwise direction (XY direction) formed by detachment of the top sheet 2 from the absorbent body 4. Therefore, it is difficult for the structural material of the absorbent body 4 to pass through the openings 10 on the clothing side of the top sheet 2, and as a result it remains in the openings 10 of the absorbent body 4 and/or between the top sheet 2 and absorbent body 4. Consequently, it is possible to prevent the structural material of the absorbent body 4 from passing through the openings 10 of the top sheet 2 and escaping to the exterior. Furthermore, since escape of the structural material of the absorbent body 4 to the exterior can be prevented even without compressing the top sheet 2 and absorbent body 4 until the top sheet formed as a film covers the side walls of the openings, it is possible to prevent increase in the density of the absorbent body by the step of opening the absorbent body.

If the opening diameter of the openings 10 on the skin side of the absorbent body 4 is represented by R3, then the opening diameter R2 mentioned above is preferably smaller than the opening diameter R3. This will make it difficult for the structural material of the absorbent body 4, such as the hydrophilic fiber and super-absorbent polymer (SAP) that have escaped through the openings 10 of the absorbent body 4, to pass through the openings 10 on the clothing side of the top sheet 2, and it will therefore remain in the openings 10 of the absorbent body 4 and/or between the top sheet 2 and absorbent body 4. As a result, it will be possible to prevent the structural material of the absorbent body 4 from passing through the openings 10 of the top sheet 2 and escaping to the exterior, since the opening diameter R2 is smaller than the opening diameter R3. Furthermore, since escape of the structural material of the absorbent body 4 to the exterior can be prevented even without compressing the top sheet 2 and absorbent body 4 until the top sheet formed as a film covers the side walls of the openings, it will be possible to prevent increase in the density of the absorbent body depending on the step of opening the absorbent body. For example, the opening diameter R2 is preferably smaller than the opening diameter R3 by just over 10% of the length of the opening diameter R3, and more preferably it is smaller by just over 30% of the length of the opening diameter R3. The opening diameter R3 is preferably 0.11 to 3.3 mm and more preferably 0.33 to 3 mm.

The opening diameter R1 of the openings 10 on the skin side of the top sheet 2 is preferably smaller than the opening diameter R3 of the openings 10 on the skin side of the absorbent body 4. This will facilitate separation of the top sheet 2 from the absorbent body 4 at the openings 10.

As mentioned above, the top sheet 2 has a blood modifying agent-coated region 8 coated with a blood modifying agent. The blood modifying agent will now be described in detail. As explained hereunder, the viscosity and surface tension of body fluid are lowered by the blood modifying agent of the blood modifying agent-coated region 8, and body fluid that has been excreted into the blood modifying agent-coated region 8 of the top sheet 2 rapidly migrates from the top sheet 2 to the absorbent body 4 and is absorbed into the absorbent body 4. This increases the absorption rate at which body fluid is absorbed into the absorbent body 4. Furthermore, since the viscosity and surface tension of highly viscous body fluid is lowered by the blood modifying agent, highly viscous body fluid does not easily remain on the top sheet 2. As a result, body fluid discharged from a wearer will not be visible from the exterior, and this can prevent the wearer from seeing the body fluid remaining on the surface of the top sheet and being left with a visually unpleasant image. In addition, it is possible to inhibit leakage of body fluid excreted by the wearer into the top sheet 2, from the widthwise direction side of the absorbent article 1.

The coating basis weight of the blood modifying agent on the top sheet 2 is preferably 1 to 30 g/m$^2$ and more preferably 3 to 10 g/m$^2$. If the coating basis weight of the blood modifying agent is smaller than 1 g/m$^2$, it may be difficult to coat the blood modifying agent on the top sheet 2 in a stable manner, while if the coating basis weight of the blood modifying agent is greater than 30 g/m$^2$, the top sheet 2 may become greasy.

After the blood modifying agent has been heated to a prescribed temperature, it is coated onto the top sheet 2 using a contact coater such as a slot coater, or a non-contact coater such as a spray coater, curtain coater or spiral coater. From the viewpoint of allowing uniform dispersion of the blood modifying agent in droplet form in the blood modifying agent-coated region 8, and avoiding damage to the top sheet 2, it is preferred to coat the blood modifying agent on the top sheet 2 using a non-contact coater.

When a nonwoven fabric is to be made for the top sheet, the nonwoven fabric may also be coated with a blood modifying agent. The top sheet 2 may also be coated with the blood modifying agent in the step of producing the absorbent article 1. However, the blood modifying agent is preferably coated on the top sheet 2 in the step of producing the absorbent article 1, since this can minimize equipment investment. Also, in order to prevent reduction in the amount of blood modifying agent coated on the top sheet 2 during the step of producing the absorbent article 1, it is preferred to coat the blood modifying agent on the top sheet 2 in a step near completion of the absorbent article 1. For example, the top sheet 2 may be coated with the blood modifying agent just before the step of wrapping the absorbent article 1.

The back sheet 3 prevents body fluid that has been absorbed into the absorbent body 4 from leaking to the outside. As the back sheet there may be used a liquid-impermeable film composed mainly of polyethylene (PE) and polypropylene (PP), an air-permeable resin film, a composite film comprising an air-permeable resin film bonded to a spunbond or spunlace nonwoven fabric, or a spunbond/melt blowing/spunbond (SMS) nonwoven fabric comprising a highly water-resistant meltblown nonwoven fabric sandwiched between high-strength spunbond nonwoven fabrics. In order to soften the absorbent article 1 so as not to impair the feel during wearing of the absorbent article 1, it is preferred to use a resin film with a basis weight of 15 to 30 g/m², composed mainly of a low-density polyethylene (LDPE) resin, for example, as the back sheet 3.

The absorbent body 4 has the function of absorbing and retaining body fluid. The absorbent body 4 preferably has high bulk, is resistant to deformation and has low chemical irritation. The absorbent body 4 used may be, for example, an absorbent body comprising hydrophilic fibers and a super-absorbent polymer (SAP), or a mixture comprising fluffy pulp or an airlaid nonwoven fabric and a super-absorbent polymer. Such an absorbent body 4 is covered with a wrap sheet 41 for use.

Hydrophilic fibers for an absorbent body 4 include cellulose such as ground pulp and cotton, regenerated cellulose such as rayon or fibril rayon, semi-synthetic cellulose such as acetate and triacetate, particulate polymers, filamentous polymers, thermoplastic hydrophobic chemical fibers, hydrophilicized thermoplastic hydrophobic chemical fibers, and mixtures of the foregoing. Cellulose foam and synthetic resin continuous foam may also be used in the absorbent body 4. Also, a foam or sheeted material may be pulverized and then molded into the absorbent body shape for use as the absorbent body 4. Preferably, ground pulp is used as the hydrophilic fibers for the absorbent body 4, in consideration of reducing cost and facilitating molding.

As super-absorbent polymers (SAP) for such an absorbent body 4 there are commonly used particulate polymers such as sodium acrylate copolymer which exhibits absorptivity and hygroscopicity. In order to impart other functions to the polymer, silver, copper, zinc, silica, active carbon, an aluminosilicate compound, zeolite or the like may also be added to the polymer. This can impart functions such as deodorant, antibacterial or heat-absorbing effects to the polymer.

The wrap sheet 41 that covers the outer side of the absorbent body 4 is not particularly restricted so long as it has liquid-permeability and a barrier property so that the polymer absorbent body does not slip. For example, a woven fabric or nonwoven fabric may be used as the wrap sheet 41. The material of the woven fabric or nonwoven fabric may be either natural fibers or chemical fibers. Examples of natural fibers include cellulose such as ground pulp and cotton. Chemical fibers include regenerated cellulose such as rayon and fibril rayon, semi-synthetic cellulose such as acetate and triacetate, thermoplastic hydrophobic chemical fibers, and hydrophilicized thermoplastic hydrophobic chemical fibers.

Web forming, as a method for fabrication of a nonwoven fabric to be used in a wrap sheet 41, may be accomplished by either a dry method (carding method, spunbond method, meltblown method or airlaid method) or wet method, or a combination of a dry method and a wet method. The method of bonding the nonwoven fabric to be used in a wrap sheet 41 may be thermal bonding, needle punching, chemical bonding or the like, with no particular restriction to these methods. Spunlace formed into a sheet by a hydroentangling method may also be used in the wrap sheet 41. The wrap sheet 41 is preferably tissue composed mainly of ground pulp and formed by a wet method, in consideration of reducing cost and increasing the barrier property.

As mentioned above, the absorbent body 4 has openings 10 running through the absorbent body 4 in the thickness direction. This will allow the absorbent body 4 to absorb body fluid discharged by the wearer not only on the skin side and clothing side of the absorbent body 4, but also in the openings 10, thereby allowing more rapid absorption of body fluid by the absorbent body 4. In addition, since the absorbent body 4 can absorb body fluid at sections near the back sheet 3 in the interiors of the openings 10, the absorbent body 4 is able to absorb body fluid at sections of the absorbent body 4 away from the skin of the wearer. This allows the wearer to comfortably wear the absorbent article even after body fluid has been excreted into the absorbent article 1. In addition, the air permeability of the absorbent article 1 is satisfactory due to the openings 10 provided in the absorbent body 4.

The number of openings 10 per 1 cm² on the skin side of the absorbent body 4 is preferably 1-10 and more preferably 1-5. If the number of openings 10 per 1 cm² on the skin side of the absorbent body 4 is less than 1, the aforementioned effect of more rapid absorption of body fluid by the openings 10 may not be obtained. Also, if the number of openings 10 per 1 cm² on the skin side of the absorbent body 4 is greater than 10, body fluid absorbed by the absorbent body 4 will not spread very much in the planar direction, and it may not be possible to absorb body fluid in a wide area on the skin side of the absorbent body 4. Also, if the number of openings 10 per 1 cm² on the skin side of the absorbent body 4 is greater than 10, the amount of absorbed body fluid that can be absorbed by the absorbent body 4 may be reduced.

The open area of the openings 10 is preferably 0.01 to 10 mm² and more preferably 0.1 to 2.5 mm². If the open area of the openings 10 is smaller than 0.01 mm², body fluid may not penetrate to the interiors of the openings 10. Also, if the open area of the openings 10 is greater than 10 mm², the aforementioned effect of more rapid absorption of body fluid by the openings 10 may not be obtained.

If the opening diameter of the openings 10 on the clothing side of the absorbent body 4 is represented as R4 (see FIG. 2($b$)), the opening diameter R4 is preferably smaller than the opening diameter R3 of the openings 10 on the skin side of the absorbent body 4. Also, the opening diameter R4 may be larger than the opening diameter R2 of the openings 10 on the clothing side of the top sheet 2, or it may be the same as the opening diameter R2, or smaller than the opening diameter R2. However, the opening diameter R4 is preferably a size of no greater than the size of the opening diameter R2, and more preferably it is smaller than the opening diameter R2. This can reduce the area of the section of the back sheet 3 that does not absorb body fluid at the openings 10. For example, the opening diameter R4, in comparison to the opening diameter R2, is preferably 0-30% smaller than the opening diameter R2. The opening diameter R4 is preferably 0.1 to 3 mm and more preferably 0.3 to 2.7 mm.

As shown in FIG. 2($b$), the interiors of the openings 10 of the absorbent body 4 are covered by the wrap sheet 41. This can minimize escape of the structural materials of the absorbent body 4 through the openings 10 of the absorbent body 4. So long as the wrap sheet 41 covers the interiors of the openings 10 to an extent allowing escape of the structural materials of the absorbent body 4 from the openings 10 of the absorbent body 4 to be minimized, the wrap sheet 41 does not need to completely cover the interiors of the openings 10, and may instead cover only portions of the interiors of the openings 10.

By combination of the magnitude relationship between the opening diameters of the openings 10 in the top sheet 2 and the absorbent body 4, and covering of the interiors of the openings 10 with the wrap sheet 41, it is possible to more reliably prevent escape of the structural material of the absorbent body 4 through the openings 10 of the absorbent body 4.

Figure 3:
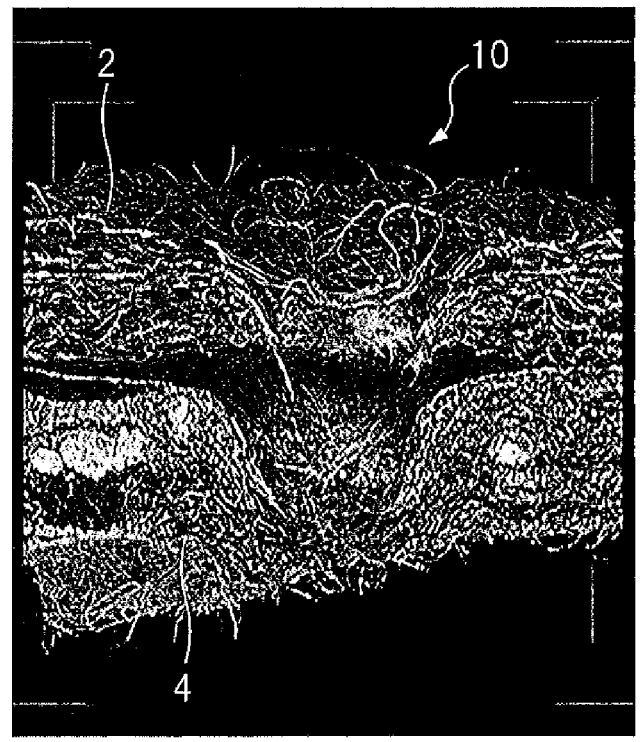
FIG. 3 is an X-ray CT photograph of an opening in an absorbent article according to an embodiment of the invention.

FIG. 3 shows an X-ray CT photograph of an opening 10 of an absorbent article 1. The top side is the top sheet, and the bottom side is the absorbent body. In this X-ray CT photograph it is seen that the top sheet is detached from the absorbent body at the openings, that the opening diameter of the opening on the skin side of the top sheet is larger than the opening diameter of the opening on the clothing side of the top sheet, that the opening diameter of the opening on the clothing side of the top sheet is smaller than the opening diameter of the opening on the skin side of the absorbent body, that the opening diameter of the opening on the skin side of the top sheet is smaller than the opening diameter of the opening on the skin side of the absorbent body, and that the opening diameter of the opening on the clothing side of the absorbent body is no greater than the size of the opening diameter of the opening on the clothing side of the top sheet. X-ray CT imaging allows non-destructive observation of the cross-section of the openings. By using X-ray CT imaging, therefore, it is possible to non-destructively observe that the top sheet is detached from the absorbent body at the openings, and to non-destructively measure the opening diameters of the openings of the top sheet and the absorbent body.

As mentioned above, the top sheet 2 has a blood modifying agent-coated region 8 coated with a blood modifying agent formed on the regions where the openings 10 have been formed. Thus, the blood modifying agent is coated not only on the top sheet 2 situated on the skin side of the absorbent body 4, but also on interiors of the openings 10. As explained hereunder, the viscosity and surface tension of body fluid excreted into the blood modifying agent-coated region 8 are lowered by the blood modifying agent of the blood modifying agent-coated region 8, and body fluid that has been excreted into the blood modifying agent-coated region 8 of the top sheet 2 rapidly migrates from the top sheet 2 to the absorbent body 4 and is absorbed into the absorbent body 4. Thus, by coating the interiors of the openings 10 with a blood modifying agent, body fluid that has permeated the openings 10 is rapidly absorbed into the absorbent body 4. In addition, since the blood modifying agent lowers the viscosity and surface tension of highly viscous body fluid, even body fluids with high viscosity and surface tension are able to migrate into the absorbent body 4. As a result, lumps of highly viscous body fluid do not easily remain in the interiors of the openings 10, and it is possible to minimize blockage of the openings 10 caused by lumps of highly viscous body fluid.

Incidentally, the blood modifying agent may be coated onto all of the openings 10 formed in the absorbent article 1, or the blood modifying agent may be coated only onto some of the openings 10 formed in the absorbent article 1.

The side sheet 5 prevents body fluid from leaking through the surface and/or interior of the top sheet 2 to the outside of the absorbent article 1 in the widthwise direction. The side sheet 5 preferably has hydrophobicity and water-repellency. A spunbond nonwoven fabric or SMS nonwoven fabric, for example, is used for the side sheet 5. In addition, since the side sheet 5 contacts with the skin of the wearer, an air-through nonwoven fabric that can reduce rubbing irritation on the skin is preferably used as the side sheet 5. The side sheet 5 is not essential, however, in the absorbent article 1.

The top sheet 2, back sheet 3, absorbent body 4 and side sheet 5 are preferably bonded together to prevent interlayer separation between them. Their bonding may be accomplished, for example, by embossing, ultrasonic waves, with a hot-melt adhesive, or by a combination of the foregoing. The top sheet 2 and back sheet 3 are bonded at a seal section 12 by embossing, for example. The back sheet 3 and side sheet 5 are also bonded at a seal section 13 by embossing, for example. The top sheet 2 and side sheet 5 are bonded by a hot-melt adhesive, for example, on both sides in the widthwise direction of the body section 6.

As an example of embossing, the top sheet and back sheet, or the top sheet and back sheet and side sheet, may be passed together between a patterned embossing roll and a flat roll, and the perimeter of the absorbent body embossed (a method known as round sealing). This will form seal sections 12,13 in the absorbent article 1. By heating the embossing roll and/or flat roll, each sheet is softened so that the seal sections 12,13 become more distinct. Emboss patterns include lattice-like patterns, zigzag patterns and wavy patterns. In order to inhibit bending of the absorbent article 1 at the borders of the seal sections 12,13, the emboss pattern is preferably intermittently elongated.

When a hot-melt adhesive is used to bond the top sheet, back sheet, absorbent body and side sheet, a hot-melt adhesive is coated onto each sheet by a coating method such as spiral coating, coater coating, curtain coater coating or Summit gun coating. The sheets are then stacked and bonded together. After the sheets have been bonded together, they may be subjected to embossing to increase the peel strength between the sheets.

Hot-melt adhesives to be used for bonding the sheets together include pressure-sensitive adhesives and heat-sensitive adhesives composed mainly of rubber-based compounds such as styrene-ethylene-butadiene-styrene (SEBS), styrene-butadiene-styrene (SBS) or styrene-isoprene-styrene (SIS), or composed mainly of olefin-based compounds such as linear low-density polyethylene, and water-sensitive adhesives such as polyvinyl alcohol, carboxylmethyl cellulose and gelatin comprising water-soluble polymers or polyvinyl acetate and sodium polyacrylate comprising water-swelling polymers. A heat-sensitive adhesive that has no tack when it has seeped out to the exterior is preferred for use as a hot-melt adhesive for bonding between the sheets. Specific examples include adhesives prepared by melt mixing of 5-25% of SEBS, 40-60% of an alicyclic saturated hydrocarbon, 1-10% of an aromatic-modified terpene and 15-35% of an additive.

The wing sections 7 are provided in the absorbent article 1 to stably anchor the absorbent article 1 to underwear. After the wing sections 7 have been folded on the outer side of the underwear, the absorbent article is attached to the crotch region of the underwear through the pressure-sensitive adhesive section 14 to allow the absorbent article 1 to be stably anchored to the underwear. The shapes of the wing sections 7 are roughly rectangular.

The pressure-sensitive adhesive section 15 on the clothing side of the back sheet 3 anchors the body section 6 to the inside of the crotch region of the underwear, and the pressure-sensitive adhesive section 14 on the clothing side of the wing sections 7 anchors the wing sections 7 to the outside of the crotch region of the underwear. The pressure-sensitive adhesive used to form the pressure-sensitive adhesive sections 14,15 is preferably, for example, one composed mainly of a styrene-based polymer, tackifier or plasticizer. Styrene-based polymers include styrene-ethylene-butylene-styrene block copolymer, styrene-butylene polymer, styrene-butylene-styrene block copolymer and styrene-isobutylene-styrene copolymer, any of which may be used alone or as polymer blends of two or more. Styrene-ethylene-butylene-styrene block copolymer is preferred as the pressure-sensitive adhesive for the pressure-sensitive adhesive sections 13,14 from the viewpoint of satisfactory thermostability.

An organic compound that is solid at ordinary temperature is preferably used as the tackifier and plasticizer. A tackifier may be, for example, a C5 petroleum resin, C9 petroleum resin, dicyclopentadiene-based petroleum resin, rosin-based petroleum resin, polyterpene resin, terpenephenol resin or the like, and a plasticizer may be, for example, a monomer plasticizer such as tricresyl phosphate, dibutyl phthalate or dioctyl phthalate, or a polymer plasticizer such as a vinyl polymer or polyester.

The blood modifying agent to be coated onto the blood modifying agent-coated region 8 will now be explained in detail. The blood modifying agent lowers the viscosity and surface tension of body fluid, and especially menstrual blood, after the highly viscous menstrual blood has been absorbed by the top sheet 2, and allows menstrual blood to rapidly migrate from the top sheet 2 into the absorbent body 4. Thus, highly viscous menstrual blood does not easily remain on the top sheet 2, and the top sheet 2 has a smooth feel without stickiness. Furthermore, since the viscosity and surface tension of highly viscous menstrual blood is lowered by the blood modifying agent and menstrual blood therefore migrates to the absorbent body 4, masses of highly viscous menstrual blood do not easily remain on the top sheet and the wearer is less easily left with a visually unpleasant image.

The blood modifying agent layer 24 will now be described in detail. The blood modifying agent of the blood modifying agent layer 24 has an IOB of about 0.00 to about 0.60, a melting point of no higher than about 45° C., and a water solubility of about 0.00 to about 0.05 g in 100 g of water at 25° C.

The IOB (Inorganic Organic Balance) is an indicator of the hydrophilic-lipophilic balance, and as used herein, it is the value calculated by the following formula by Oda et al.:

IOB=inorganic value/organic value.

The inorganic value and the organic value are based on the organic paradigm described in "Organic compound predictions and organic paradigms" by Fujita A., Kagaku no Ryoiki (Journal of Japanese Chemistry), Vol. 11, No. 10 (1957) p. 719-725 which is incorporated by reference herein.

The organic values and inorganic values of major groups, according to Fujita, are summarized in Table 1 below.

TABLE 1

| Group | Inorganic value | Organic value |
|---|---|---|
| —COOH | 150 | 0 |
| —OH | 100 | 0 |
| —O—CO—O— | 80 | 0 |
| —CO— | 65 | 0 |
| —COOR | 60 | 0 |
| —O— | 20 | 0 |
| Triple bond | 3 | 0 |
| Double bond | 2 | 0 |
| $CH_2$ | 0 | 20 |
| iso-branch | 0 | −10 |
| tert-branch | 0 | −20 |
| Light metal (salt) | ≥500 | 0 |
| Heavy metal (salt), amine, $NH_3$ salt | ≥400 | 0 |

For example, in the case of an ester of tetradecanoic acid which has 14 carbon atoms and dodecyl alcohol which has 12 carbon atoms, the organic value is 520 ($CH_2$, 20×26) and the inorganic value is 60 (—COOR, 60×1), and therefore IOB=0.12.

In the blood modifying agent, the IOB is about 0.00-0.60, preferably about 0.00-0.50, more preferably about 0.00-0.40 and even more preferably about 0.00-0.30. This is because a lower IOB is associated with higher organicity and higher affinity with blood cells.

As used herein, the term "melting point" refers to the peak top temperature for the endothermic peak during conversion from solid to liquid, upon measurement with a differential scanning calorimetry analyzer at a temperature-elevating rate of 10° C./min. The melting point may be measured using a Model DSC-60 DSC measuring apparatus by Shimadzu Corp., for example.

If the blood modifying agent has a melting point of no higher than about 45° C., it may be either liquid or solid at room temperature, or in other words, the melting point may be either about 25° C. or higher or below about 25° C., and for example, it may have a melting point of about −5° C. or about −20° C. The reason for a melting point of no higher than about 45° C. for the blood modifying agent will be explained below.

The blood modifying agent does not have a lower limit for its melting point, but its vapor pressure is preferably low. The vapor pressure of the blood modifying agent is preferably between about 0.00 and about 0.01 Pa, more preferably between about 0.000 and about 0.001 Pa and even more preferably between about 0.0000 and about 0.0001 Pa, at 1 atmosphere, 25° C. Considering that the absorbent article of the present disclosure is to be used in contact with the human body, the vapor pressure is preferably between about 0.00 and about 0.01 Pa, more preferably between about 0.000 and about 0.001 Pa and even more preferably between about 0.0000 and about 0.0001 Pa, at 1 atmosphere, 40° C. If the vapor pressure is high, gasification may occur during storage and the amount of blood modifying agent may be reduced, often creating problems such as odor during wear.

The melting point of the blood modifying agent may also differ depending on the weather or duration of wear. For example, in regions with a mean atmospheric temperature of no higher than about 10° C., using a blood modifying agent with a melting point of no higher than about 10° C. may allow the blood modifying agent to stably modify blood after excretion of menstrual blood, even if it has been cooled by the ambient temperature.

Also, as the absorbent article may be used for a prolonged period of time, the melting point of the blood modifying agent is preferably at the high end of the range of no higher than about 45° C. This is because the blood modifying agent is not easily affected by sweat or friction during wearing, and will not easily migrate even during prolonged wearing.

The water solubility of 0.00-0.05 g may be measured by adding 0.05 g of sample to 100 g of deionized water at 25° C., allowing it to stand for 24 hours, and after 24 hours, gently stirring if necessary, and then visually evaluating whether or not the sample has dissolved.

As used herein, the term "solubility" in regard to water solubility includes cases where the sample completely dissolves in deionized water to form a homogeneous mixture, and cases where the sample is completely emulsified. As used herein, "completely" means that no mass of the sample remains in the deionized water.

When top sheet surfaces are coated with surfactants in order to alter the surface tension of blood and promote the rapid absorption of blood, because surfactants generally have high water solubility, the surfactant-coated top sheet is highly miscible with hydrophilic components (such as blood plasma) in the blood and therefore, instead, they tend to cause residue of blood on the top sheet. The aforementioned blood modifying agent has low water solubility and therefore, it does not cause residue of blood on the top sheet and allows rapid migration into the absorbent body.

As used herein, a water solubility of water at 25° C. may be simply referred to as "water solubility".

As used herein, "weight-average molecular weight" includes the concept of a polydisperse compound (for example, a compound produced by stepwise polymerization, an ester formed from a plurality of fatty acids and a plurality of aliphatic monohydric alcohols), and a simple compound (for example, an ester formed from one fatty acid and one aliphatic monohydric alcohol), and in a system comprising $N_i$ molecules with molecular weight $M_i$ (i=1, or i=1, 2 . . . ), it refers to $M_w$ determined by the following formula.

$$M_w = \Sigma N_i M_i^2 / \Sigma N_i M_i$$

As used herein, the weight-average molecular weights are the values measured by gel permeation chromatography (GPC), based on polystyrene.

The GPC measuring conditions may be the following, for example.

Device: Lachrom Elite high-speed liquid chromatogram by Hitachi High-Technologies Corp.

Columns: SHODEX KF-801, KF-803 and KF-804, by Showa Denko K.K.

Eluent: THF

Flow rate: 1.0 mL/min

Driving volume: 100 μL

Detection: RI (differential refractometer)

The weight-average molecular weights listed in the examples of the present specification were measured under the conditions described below.

Preferably, the blood modifying agents is selected from the group consisting of the following items (i)-(iii), and any combination thereof:

(i) a hydrocarbon;

(ii) a compound having (ii-1) a hydrocarbon moiety, and (ii-2) one or more groups each selected from the group consisting of carbonyl group (—CO—) and oxy group (—O—) inserted between a C—C single bond of the hydrocarbon moiety; and (iii) a compound having (iii-1) a hydrocarbon moiety, (iii-2) one or more groups each selected from the group consisting of carbonyl group (—CO—) and oxy group (—O—) inserted between a C—C single bond of the hydrocarbon moiety, and (iii-3) one or more groups each selected from the group consisting of carboxyl group (—COOH) and hydroxyl group (—OH) substituting a hydrogen of the hydrocarbon moiety.

As used herein, "hydrocarbon" refers to a compound composed of carbon and hydrogen, and it may be a chain hydrocarbon, such as a paraffinic hydrocarbon (containing no double bond or triple bond, also referred to as alkane), an olefin-based hydrocarbon (containing one double bond, also referred to as alkene), an acetylene-based hydrocarbon (containing one triple bond, also referred to as alkyne), or a hydrocarbon comprising two or more bonds each selected from the group consisting of double bonds and triple bonds, and cyclic hydrocarbon, such as aromatic hydrocarbons and alicyclic hydrocarbons.

Preferred as such hydrocarbons are chain hydrocarbons and alicyclic hydrocarbons, with chain hydrocarbons being more preferred, paraffinic hydrocarbons, olefin-based hydrocarbons and hydrocarbons with two or more double bonds (containing no triple bond) being more preferred, and paraffinic hydrocarbons being even more preferred.

Chain hydrocarbons include linear hydrocarbons and branched hydrocarbons.

When two or more oxy group (—O—) are inserted in the compounds of (ii) and (iii) above, the oxy group (—O—) are not adjacent to each other. Thus, compounds (ii) and (iii) do not include compounds with continuous oxy group (i.e., peroxides).

In the compounds of (iii), compounds in which at least one hydrogen on the hydrocarbon moiety is substituted with a hydroxyl group (—OH) are more preferred than compounds in which at least one hydrogen on the hydrocarbon moiety is substituted with a carboxyl group (—COOH). As shown in Table 1, the carboxyl groups bond with metals and the like in menstrual blood, drastically increasing the inorganic value from 150 to 400 or greater, and therefore a blood modifying agent with carboxyl groups can increase the IOB value to more than about 0.6 during use, potentially lowering the affinity with blood cells.

More preferably, the blood modifying agent is a compound selected from the group consisting of the following items (i')-(iii'), and any combination thereof:

(i') a hydrocarbon;

(ii') a compound having at least (ii'-1) a hydrocarbon moiety, and (ii'-2) one or more bonds each selected from the group consisting of carbonyl bond (—CO—), at least one ester bond (—COO—), at least one carbonate bond (—OCOO—), and/or at least one ether bond (—O—) inserted between a C—C single bond of the hydrocarbon moiety; and (iii') a compound having at least (iii'-1) a hydrocarbon moiety, (iii'-2) one or more bonds each selected from the group consisting of carbonyl bond (—CO—), at least one ester bond (—COO—), at least one carbonate bond (—OCOO—), and/or at least one ether bond (—O—) inserted between a C—C single bond of a hydrocarbon, and (iii'-3) one or more groups each selected from the group consisting of carboxyl group (—COOH) and hydroxyl group (—OH) substituting a hydrogen on the hydrocarbon moiety.

When 2 or more same or different bonds are inserted in the compound of (ii') or (iii'), i.e., when 2 or more bonds each selected from the group consisting of carbonyl bonds (—CO—), ester bonds (—COO—), carbonate bonds (—OCOO—) and ether bonds (—O—) are inserted, the bonds are not adjacent to each other, and at least one carbon atom lies between each of the bonds.

The blood modifying agent is more preferably a compound with no more than about 1.8 carbonyl bonds (—CO—), no more than 2 ester bonds (—COO—), no more than about 1.5 carbonate bonds (—OCOO—), no more than about 6 ether bonds (—O—), no more than about 0.8 carboxyl groups (—COOH) and/or no more than about 1.2 hydroxyl groups (—OH), per 10 carbon atoms in the hydrocarbon moiety.

Even more preferably, the blood modifying agent may also be selected from the group consisting of the following items (A)-(F), and any combination thereof:

(A) an ester of (A1) a compound having a chain hydrocarbon moiety and 2-4 hydroxyl groups substituting hydrogens on the chain hydrocarbon moiety, and (A2) a compound having a chain hydrocarbon moiety and 1 carboxyl group substituting a hydrogen on the chain hydrocarbon moiety;

(B) an ether of (B1) a compound having a chain hydrocarbon moiety and 2-4 hydroxyl groups substituting hydrogens on the chain hydrocarbon moiety and (B2) a compound having a chain hydrocarbon moiety and 1 hydroxyl group substituting a hydrogen on the chain hydrocarbon moiety;

(C) an ester of (C1) a carboxylic acid, hydroxy acid, alkoxy acid or oxoacid comprising a chain hydrocarbon moiety and 2-4 carboxyl groups substituting hydrogens on the chain hydrocarbon moiety and (C2) a compound having a chain hydrocarbon moiety and 1 hydroxyl group substituting a hydrogen on the chain hydrocarbon moiety;

(D) a compound having a chain hydrocarbon moiety and one bond selected from the group consisting of ether bonds (—O—), carbonyl bonds (—CO—), ester bonds (—COO—) and carbonate bonds (—OCOO—) inserted in-between a C—C single bond of the chain hydrocarbon moiety;

(E) a polyoxy $C_2$-$C_6$ alkylene glycol, or alkyl ester or alkyl ether thereof; and (F) a chain hydrocarbon.

The blood modifying agent in accordance with (A) to (F) will now be described in detail.

[(A) Ester of (A1) a Compound Having a Chain Hydrocarbon Moiety and 2-4 Hydroxyl Groups Substituting Hydrogens on the Chain Hydrocarbon Moiety, and (A2) a Compound Having a Chain Hydrocarbon Moiety and 1 Carboxyl Group Substituting a Hydrogen on the Chain Hydrocarbon Moiety]

The (A) ester of (A1) a compound having a chain hydrocarbon moiety and 2-4 hydroxyl groups substituting hydrogens on the chain hydrocarbon moiety, and (A2) a compound having a chain hydrocarbon moiety and 1 carboxyl group substituting a hydrogen on the chain hydrocarbon moiety (hereunder also referred to as "compound (A)") includes esters of a compound with 4, 3 or 2 hydroxyl groups and a compound with 1 carboxyl group, and it is not necessary for all of the hydroxyl groups to be esterified so long as the IOB, melting point and water solubility are within the aforementioned ranges.

Examples of (A1) a compound having a chain hydrocarbon moiety and 2-4 hydroxyl groups substituting hydrogens on the chain hydrocarbon moiety (hereunder also referred to as "compound (A1)") include chain hydrocarbon tetraols such as alkanetetraols, including pentaerythritol, chain hydrocarbon triols such as alkanetriols, including glycerins, and chain hydrocarbon diols such as alkanediols, including glycols. Examples of (A2) a compound having a chain hydrocarbon moiety and 1 carboxyl group substituting a hydrogen on the chain hydrocarbon moiety (hereunder also referred to as "compound (A2)") include compounds in which one hydrogen on the hydrocarbon is substituted with one carboxyl group (—COOH), such as fatty acids.

Examples for compound (A) include ($a_1$) an ester of a chain hydrocarbon tetraol and at least one fatty acid, ($a_2$) an ester of a chain hydrocarbon triol and at least one fatty acid, and ($a_3$) an ester of a chain hydrocarbon diol and at least one fatty acids.

[($a_1$) Ester of a Chain Hydrocarbon Tetraol and at Least One Fatty Acid]

Examples of an ester of a chain hydrocarbon tetraol and at least one fatty acid include tetraesters of pentaerythritol and fatty acids, represented by the following formula (1):

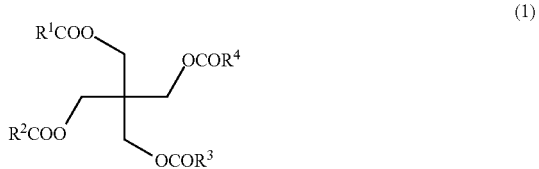

(1)

triesters of pentaerythritol and fatty acids, represented by the following formula (2):

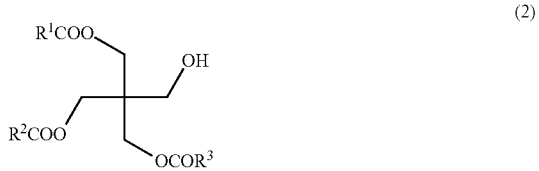

(2)

diesters of pentaerythritol and fatty acids, represented by the following formula (3):

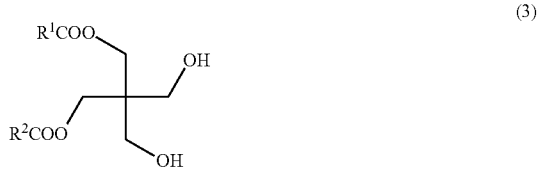

(3)

and monoesters of pentaerythritol and fatty acids, represented by the following formula (4).

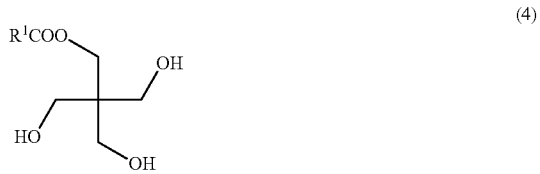

(4)

In the formulae, $R^1$-$R^4$ each represent a chain hydrocarbon.

The fatty acids composing the esters of pentaerythritol and fatty acids ($R^1$COOH, $R^2$COOH, $R^3$COOH, and $R^4$COOH) are not particularly restricted as long as the pentaerythritol and fatty acid esters satisfy the conditions for the IOB, melting point and water solubility, and for example, there may be mentioned saturated fatty acids, such as $C_2$-$C_{30}$ saturated fatty acids, including acetic acid ($C_2$) ($C_2$ representing the number of carbons, corresponding to the number of carbons of each of $R^1C$, $R^2C$, $R^3C$ or $R^4C$, same hereunder), propanoic acid ($C_3$), butanoic acid ($C_4$) and isomers thereof such as 2-methylpropanoic acid ($C_4$), pentanoic acid ($C_5$) and isomers thereof such as 2-methylbutanoic acid ($C_5$) and 2,2-dimethylpropanoic acid ($C_5$), hexanoic acid ($C_6$), heptanoic acid ($C_7$), octanoic acid ($C_8$) and isomers thereof, such as 2-ethylhexanoic acid ($C_8$), nonanoic acid ($C_9$), decanoic acid ($C_{10}$), dodecanoic acid ($C_{12}$), tetradecanoic acid ($C_{14}$), hexadecanoic acid ($C_{16}$), heptadecanoic acid ($C_{17}$), octadecanoic acid ($C_{18}$), eicosanoic acid ($C_{20}$), docosanoic acid ($C_{22}$), tetracosanoic acid ($C_{24}$), hexacosanoic acid ($C_{26}$), octacosanoic acid ($C_{28}$) and triacontanoic acid ($C_{30}$), as well as isomers of the foregoing (excluding those mentioned above).

The fatty acid may also be an unsaturated fatty acid. Examples of unsaturated fatty acids include $C_3$-$C_{20}$ unsaturated fatty acids, such as monounsaturated fatty acids including crotonic acid ($C_4$), myristoleic acid ($C_{14}$), palmitoleic acid ($C_{16}$), oleic acid ($C_{18}$), elaidic acid ($C_{18}$), vaccenic acid ($C_{18}$), gadoleic acid ($C_{20}$) and eicosenoic acid ($C_{20}$), di-unsaturated fatty acids including linolic acid ($C_{18}$) and eicosadienoic acid ($C_{20}$), tri-unsaturated fatty acids including linolenic acids, such as α-linolenic acid ($C_{18}$) and γ-linolenic acid ($C_{18}$), pinolenic acid ($C_{18}$), eleostearic acids, such as α-eleostearic acid ($C_{18}$) and β-eleostearic acid ($C_{18}$), Mead acid ($C_{20}$), dihomo-γ-linolenic acid ($C_{20}$) and eicosatrienoic acid ($C_{20}$), tetra-unsaturated fatty acids including stearidonic acid ($C_{20}$), arachidonic acid ($C_{20}$) and eicosatetraenoic acid ($C_{20}$), penta-unsaturated fatty acids including bosseopentaenoic acid ($C_{18}$) and eicosapentaenoic acid ($C_{20}$), and partial hydrogen adducts of the foregoing.

Considering the potential for degradation by oxidation and the like, the ester of pentaerythritol and a fatty acid is preferably an ester of pentaerythritol and a fatty acid, which is derived from a saturated fatty acid, i.e., an ester of pentaerythritol and a saturated fatty acid.

Also, in order to lower the IOB and result in greater hydrophobicity, the ester of pentaerythritol and a fatty acid is preferably a diester, triester or tetraester, more preferably a triester or tetraester, and even more preferably a tetraester.

In a tetraester of pentaerythritol and a fatty acid, the IOB is 0.60 if the total number of carbons of the fatty acid composing the tetraester of the pentaerythritol and fatty acid, i.e., the total number of carbons of the $R^1C$, $R^2C$, $R^3C$ and $R^4C$ portions in formula (1), is 15. Thus, when the total number of carbons of the fatty acid composing the tetraester of the pentaerythritol and fatty acid is approximately 15 or greater, the IOB satisfies the condition of being within about 0.00 to 0.60.

Examples of tetraesters of pentaerythritol and fatty acids include tetraesters of pentaerythritol with hexanoic acid ($C_6$), heptanoic acid ($C_7$), octanoic acid ($C_8$) such as 2-ethylhexanoic acid ($C_8$), nonanoic acid ($C_9$), decanoic acid ($C_{10}$) and/or dodecanoic acid ($C_{12}$).

In a triester of pentaerythritol and a fatty acid, the IOB is 0.58 if the total number of carbons of the fatty acid composing the triester of the pentaerythritol and fatty acid, i.e., the total number of carbons of the $R^1C$, $R^2C$ and $R^3C$ portions in formula (2), is 19. Thus, when the total number of carbons of the fatty acid composing the triester of the pentaerythritol and fatty acid is approximately 19 or greater, the IOB satisfies the condition of being within about 0.00 to 0.60.

In a diester of pentaerythritol and a fatty acid, the IOB is 0.59 if the total number of carbons of the fatty acid composing the diester of the pentaerythritol and fatty acid, i.e., the total number of carbons of the $R^1C$ or $R^2C$ portion in formula (3), is 22. Thus, when the total number of carbons of the fatty acid composing the diester of the pentaerythritol and fatty acid is approximately 22 or greater, the IOB satisfies the condition of being within about 0.00 to 0.60.

In a monoester of pentaerythritol and a fatty acid, the IOB is 0.60 if the total number of carbons of the fatty acid composing the monoester of the pentaerythritol and fatty acid, i.e., the total number of carbons of the $R^1C$ portion in formula (4), is 25. Thus, when the number of carbons of the fatty acid composing the monoester of the pentaerythritol and fatty acid is approximately 25 or greater, the IOB satisfies the condition of being within about 0.00 to 0.60.

The effects of double bonds, triple bonds, iso-branches and tert-branches are not considered in this calculation.

Commercial products which are esters of pentaerythritol and fatty acids include UNISTAR H-408BRS and H-2408BRS-22 (mixed product) (both products of NOF Corp.).

[($a_2$) Ester of a Chain Hydrocarbon Triol and at Least One Fatty Acid]

Examples of esters of a chain hydrocarbon triol and at least one fatty acid include triesters of glycerin and fatty acids, represented by formula (5):

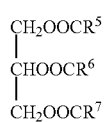

(5)

diesters of glycerin and fatty acids, represented by the following formula (6):

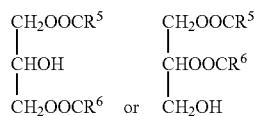

(6)

and monoesters of glycerin and fatty acids, represented by the following formula (7):

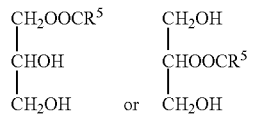

(7)

wherein $R^5$-$R^7$ each represent a chain hydrocarbon.

The fatty acid composing the ester of glycerin and a fatty acid ($R^5COOH$, $R^6COOH$ and $R^7COOH$) is not particularly restricted so long as the ester of glycerin and a fatty acid satisfies the conditions for the IOB, melting point and water solubility, and for example, there may be mentioned that the fatty acids mentioned for the "($a_1$) Ester of chain hydrocarbon tetraol and at least one fatty acids", namely saturated fatty acids and unsaturated fatty acids, and in consideration of the potential for degradation by oxidation and the like, the ester is preferably a glycerin and fatty acid ester, which is derived from a saturated fatty acid, i.e., an ester of glycerin and a saturated fatty acid.

Also, in order to lower the IOB and result in greater hydrophobicity, the ester of glycerin and a fatty acid is preferably a diester or triester, and more preferably a triester.

A triester of glycerin and a fatty acid is also known as a triglyceride, and examples include triesters of glycerin and octanoic acid ($C_8$), triesters of glycerin and decanoic acid ($C_{10}$), triesters of glycerin and dodecanoic acid ($C_{12}$), triesters of glycerin and 2 or more different fatty acids, and mixtures of the foregoing.

Examples of triesters of glycerin and 2 or more fatty acids include triesters of glycerin with octanoic acid ($C_8$) and decanoic acid ($C_{10}$), triesters of glycerin with octanoic acid ($C_8$), decanoic acid ($C_{10}$) and dodecanoic acid ($C_{12}$), and triesters of glycerin with octanoic acid ($C_8$), decanoic acid ($C_{10}$), dodecanoic acid ($C_{12}$), tetradecanoic acid ($C_{14}$), hexadecanoic acid ($C_{16}$) and octadecanoic acid ($C_{18}$).

In order to obtain a melting point of no higher than about 45° C., preferred triesters of glycerin and fatty acids are those with no more than about 40 as the total number of carbons of the fatty acid composing the triester of glycerin and the fatty acid, i.e., the total number of carbons of the $R^5C$, $R^6C$ and $R^7C$ portions in formula (5).

In a triester of glycerin and a fatty acid, the IOB value is 0.60 when the total number of carbons of the fatty acid composing the triester of glycerin and the fatty acid, i.e., the total number of carbons of the $R^5C$, $R^6C$ and $R^7C$ portions in formula (5), is 12. Thus, when the total number of carbons of the fatty acid comprising the triester of the glycerin and fatty acid is approximately 12 or greater, the IOB satisfies the condition of being within about 0.00 to 0.60.

Triesters of glycerin and fatty acids, being aliphatic and therefore potential constituent components of the human body are preferred from the viewpoint of safety.

Commercial products of triesters of glycerin and fatty acids include tri-coconut fatty acid glycerides, NA36, PAN- ACET 800, PANACET 800B and PANACET 810S, and tri-C2L oil fatty acid glycerides and tri-CL oil fatty acid glycerides (all products of NOF Corp.).

A diester of glycerin and a fatty acid is also known as a diglyceride, and examples include diesters of glycerin and decanoic acid ($C_{10}$), diesters of glycerin and dodecanoic acid ($C_{12}$), diesters of glycerin and hexadecanoic acid ($C_{16}$), diesters of glycerin and 2 or more different fatty acids, and mixtures of the foregoing.

In a diester of glycerin and a fatty acid, the IOB is 0.58 if the total number of carbons of the fatty acid composing the diester of the glycerin and fatty acid, i.e., the total number of carbons of the $R^5C$ and $R^6C$ portions in formula (6), is 16. Thus, when the total number of carbons of the fatty acid composing the diester of the glycerin and fatty acid is approximately 16 or greater, the IOB satisfies the condition of being about 0.00 to 0.60.

Monoesters of glycerin and fatty acids are also known as monoglycerides, and examples include glycerin and icosanoic acid ($C_{20}$) monoester, and glycerin and docosanoic acid ($C_{22}$) monoester.

In a monoester of glycerin and a fatty acid, the IOB is 0.59 if the number of carbons of the fatty acid composing the monoester of the glycerin and fatty acid, i.e., the number of carbons of the $R^5C$ portion in formula (7), is 19. Thus, when the number of carbons of the fatty acid composing the monoester of the glycerin and fatty acid is approximately 19 or greater, the IOB satisfies the condition of being about 0.00 to 0.60.

[($a_3$) Ester of Chain Hydrocarbon Diol and at Least One Fatty Acid]

Examples of an ester of a chain hydrocarbon diol and at least one fatty acids include monoesters and diesters of fatty acids with $C_2$-$C_6$ chain hydrocarbon diols, such as $C_2$-$C_6$ glycols, including ethylene glycol, propylene glycol, butylene glycol, pentylene glycol and hexylene glycol.

Specifically, examples of an ester of a chain hydrocarbon diol and at least one fatty acid include diesters of $C_2$-$C_6$ glycols and fatty acids, represented by the following formula (8):

wherein k represents an integer of 2-6, and $R^8$ and $R^9$ each represent a chain hydrocarbon, and monoesters of $C_2$-$C_6$ glycols and fatty acids, represented by the following formula (9):

wherein k represents an integer of 2-6, and $R^8$ is a chain hydrocarbon.

The fatty acid to be esterified in an ester of a $C_2$-$C_6$ glycol and a fatty acid (corresponding to $R^8COOH$ and $R^9COOH$ in formula (8) and formula (9)) is not particularly restricted so long as the ester of the $C_2$-$C_6$ glycol and fatty acid satisfies the conditions for the IOB, melting point and water solubility, and for example, there may be mentioned that the fatty acids mentioned for the "($a_1$) Ester of a chain hydrocarbon tetraol and at least one fatty acid", namely saturated fatty acids and unsaturated fatty acids, and in consideration of the potential for degradation by oxidation and the like, it is preferably a saturated fatty acid.

In a diester of butylene glycol (k=4) and a fatty acid represented by formula (8), IOB is 0.60 when the total number of carbons of the $R^8C$ and $R^9C$ portions is 6. Thus, when the total number of carbon atoms in a diester of butylene glycol (k=4) and a fatty acid represented by formula (8) is approximately 6 or greater, the IOB satisfies the condition of being about 0.00-0.60. In a monoester of ethylene glycol (k=2) and a fatty acid represented by formula (9), IOB is 0.57 when the number of carbons of the $R^8C$ portion is 12. Thus, when the total number of carbon atoms in the fatty acid composing a monoester of ethylene glycol (k=2) and a fatty acid represented by formula (9) is approximately 12 or greater, the IOB satisfies the condition of being about 0.00-0.60.

Considering the potential for degradation by oxidation and the like, the ester of the $C_2$-$C_6$ glycol and fatty acid is preferably a $C_2$-$C_6$ glycol and fatty acid ester, which is derived from a saturated fatty acid, i.e., an ester of a $C_2$-$C_6$ glycol and a saturated fatty acid.

Also, in order to lower the IOB and result in greater hydrophobicity, the ester of the $C_2$-$C_6$ glycol and fatty acid is preferably a glycol and fatty acid ester derived from a glycol with a greater number of carbons, such as an ester of a glycol and a fatty acid derived from butylene glycol, pentylene glycol or hexylene glycol.

Also, in order to lower the IOB and obtain in greater hydrophobicity, the ester of a $C_2$-$C_6$ glycol and fatty acid is preferably a diester.

Examples of commercial products of esters of $C_2$-$C_6$ glycols and fatty acids include COMPOL BL and COMPOL BS (both products of NOF Corp.).

[(B) Ether of (B1) a Compound Having a Chain Hydrocarbon Moiety and 2-4 Hydroxyl Groups Substituting Hydrogens on the Chain Hydrocarbon Moiety and (B2) a Compound Having a Chain Hydrocarbon Moiety and 1 Hydroxyl Group Substituting a Hydrogen on the Chain Hydrocarbon Moiety]

The (B) ether of (B1) a compound having a chain hydrocarbon moiety and 2-4 hydroxyl groups substituting hydrogens on the chain hydrocarbon moiety and (B2) a compound having a chain hydrocarbon moiety and 1 hydroxyl group substituting a hydrogen on the chain hydrocarbon moiety (hereunder also referred to as "compound (B)") includes ethers of a compound with 4, 3 or 2 hydroxyl groups and a compound with 1 hydroxyl group, and it is not necessary for all of the hydroxyl groups to be etherified as long as the IOB, melting point and water solubility are within the aforementioned ranges.

Examples of (B1) a compound having a chain hydrocarbon moiety and 2-4 hydroxyl groups substituting hydrogens on the chain hydrocarbon moiety (hereunder also referred to as "compound (B1)") include those mentioned for "compound (A)"," as compound (A1), such as pentaerythritol, glycerin and glycol.

Examples of (B2) a compound having a chain hydrocarbon moiety and 1 hydroxyl group substituting a hydrogen on the chain hydrocarbon moiety (hereunder also referred to as "compound (B2)") include compounds wherein 1 hydrogen on the hydrocarbon is substituted with 1 hydroxyl group (—OH), such as aliphatic monohydric alcohols, including saturated aliphatic monohydric alcohols and unsaturated aliphatic monohydric alcohols.

Examples of saturated aliphatic monohydric alcohols include $C_1$-$C_{20}$ saturated aliphatic monohydric alcohols, such as methyl alcohol ($C_1$) ($C_1$ representing the number of carbon atoms, same hereunder), ethyl alcohol ($C_2$), propyl alcohol ($C_3$) and isomers thereof, including isopropyl alcohol ($C_3$), butyl alcohol ($C_4$) and isomers thereof, including sec-butyl alcohol ($C_4$) and tert-butyl alcohol ($C_4$), pentyl alcohol ($C_5$), hexyl alcohol ($C_6$), heptyl alcohol ($C_7$), octyl alcohol ($C_8$) and isomers thereof, including 2-ethylhexyl alcohol ($C_8$), nonyl alcohol ($C_9$), decyl alcohol ($C_{10}$), dodecyl alcohol ($C_{12}$), tetradecyl alcohol ($C_{14}$), hexadecyl alcohol ($C_{16}$), heptadecyl alcohol ($C_{17}$), octadecyl alcohol ($C_{18}$) and eicosyl alcohol ($C_{20}$), as well as their isomers other than those mentioned.

Unsaturated aliphatic monohydric alcohols include those wherein 1 C—C single bond of a saturated aliphatic monohydric alcohol mentioned above is replaced with a C=C double bond, such as oleyl alcohol, and for example, these are commercially available by New Japan Chemical Co., Ltd. as the RIKACOL Series and UNJECOL Series.

Examples for compound (B) include ($b_1$) an ether of a chain hydrocarbon tetraol and at least one aliphatic monohydric alcohol, such as monoethers, diethers, triethers and tetraethers, preferably diethers, triethers and tetraethers, more preferably triethers and tetraethers and even more preferably tetraethers, ($b_2$) an ether of a chain hydrocarbon triol and at least one aliphatic monohydric alcohol, such as monoethers, diethers and triethers, preferably diethers and triethers and more preferably triethers, and ($b_3$) an ether of a chain hydrocarbon diol and at least one aliphatic monohydric alcohols, such as monoethers and diethers, and preferably diethers.

Examples of an ether of a chain hydrocarbon tetraol and at least one aliphatic monohydric alcohols include tetraethers, triethers, diethers and monoethers of pentaerythritol and aliphatic monohydric alcohols, represented by the following formulae (10)-(13):

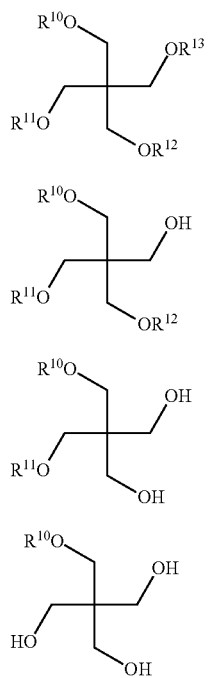

wherein $R^{10}$-$R^{13}$ each represent a chain hydrocarbon.

Examples of an ether of a chain hydrocarbon triol and at least one aliphatic monohydric alcohol include triethers, diethers and monoethers of glycerin and aliphatic monohydric alcohols, represented by the following formulae (14)-(16):

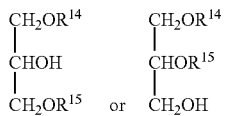 (14)

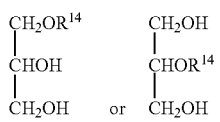 (15)

$$\begin{array}{ccc} CH_2OR^{14} & & CH_2OH \\ | & & | \\ CHOH & & CHOR^{14} \\ | & & | \\ CH_2OH & \text{or} & CH_2OH \end{array} \quad (16)$$

wherein $R^{14}$-$R^{16}$ each represent a chain hydrocarbon.

Examples of an ether of a chain hydrocarbon diol and at least one aliphatic monohydric alcohol include diethers of $C_2$-$C_6$ glycols and aliphatic monohydric alcohols, represented by the following formula (17):

$$R^{17}OC_nH_{2n}OR^{18} \quad (17)$$

wherein n is an integer of 2-6, and $R^{17}$ and $R^{18}$ are each a chain hydrocarbon, and monoethers of $C_2$-$C_6$ glycols and aliphatic monohydric alcohols, represented by the following formula (18):

$$R^{17}OC_nH_{2n}OH \quad (18)$$

wherein n is an integer of 2-6, and $R^{17}$ is a chain hydrocarbon.

In the tetraether of pentaerythritol and an aliphatic monohydric alcohol, the IOB is 0.44 when the total number of carbon atoms of the aliphatic monohydric alcohol composing the tetraether of pentaerythritol and the aliphatic monohydric alcohol, i.e., the total number of carbon atoms of the $R^{10}$, $R^{11}$, $R^{12}$ and $R^{13}$ portions in formula (10), is 4. Thus, when the total number of carbon atoms of the aliphatic monohydric alcohol composing a tetraether of pentaerythritol and an aliphatic monohydric alcohol is approximately 4 or greater, the IOB value satisfies the condition of being within about 0.00 to 0.60.

In the triether of pentaerythritol and an aliphatic monohydric alcohol, the IOB is 0.57 when the total number of carbon atoms of the aliphatic monohydric alcohol composing the triether of pentaerythritol and the aliphatic monohydric alcohol, i.e., the total number of carbon atoms of the $R^{10}$, $R^{11}$ and $R^{12}$ portions in formula (11), is 9. Thus, when the total number of carbon atoms of the aliphatic monohydric alcohol composing a triether of pentaerythritol and an aliphatic monohydric alcohol is approximately 9 or greater, the IOB value satisfies the condition of being within about 0.00 to 0.60.

In the diether of pentaerythritol and an aliphatic monohydric alcohol, the IOB is 0.60 when the total number of carbon atoms of the aliphatic monohydric alcohol composing the diether of pentaerythritol and the aliphatic monohydric alcohol, i.e., the total number of carbon atoms of the $R^{10}$ and $R^{11}$ portions in formula (12), is 15. Thus, when the total number of carbon atoms of the aliphatic monohydric alcohol composing a diether of pentaerythritol and an aliphatic monohydric alcohol is approximately 15 or greater, the IOB value satisfies the condition of being within about 0.00 to 0.60.

In the monoether of pentaerythritol and an aliphatic monohydric alcohol, the IOB is 0.59 when the number of carbon atoms of the aliphatic monohydric alcohol composing the monoether of pentaerythritol and the aliphatic monohydric alcohol, i.e., the number of carbon atoms of the $R^{10}$ portion in formula (13), is 22. Thus, when the number of carbon atoms of the aliphatic monohydric alcohol comprising a monoether of pentaerythritol and an aliphatic monohydric alcohol is approximately 22 or greater, the IOB value satisfies the condition of being within about 0.00 to 0.60.

In the triether of glycerin and an aliphatic monohydric alcohol, the IOB is 0.50 when the total number of carbon atoms of the aliphatic monohydric alcohol composing the triether of glycerin and the aliphatic monohydric alcohol, i.e., the total number of carbon atoms of the $R^{14}$, $R^{15}$ and $R^{16}$ portions in formula (14), is 3. Thus, when the total number of carbon atoms of the aliphatic monohydric alcohol comprising a triether of glycerin and an aliphatic monohydric alcohol is approximately 3 or greater, the IOB value satisfies the condition of being within about 0.00 to 0.60.

In the diether of glycerin and an aliphatic monohydric alcohol, the IOB is 0.58 when the total number of carbon atoms of the aliphatic monohydric alcohol composing the diether of glycerin and the aliphatic monohydric alcohol, i.e., the total number of carbon atoms of the $R^{14}$ and $R^{15}$ portions in formula (15), is 9. Thus, when the total number of carbon atoms of the aliphatic monohydric alcohol comprising a diether of glycerin and an aliphatic monohydric alcohol is approximately 9 or greater, the IOB value satisfies the condition of being within about 0.00 to 0.60.

In the monoether of glycerin and an aliphatic monohydric alcohol, the IOB is 0.58 when the number of carbon atoms of the aliphatic monohydric alcohol composing the monoether of glycerin and the aliphatic monohydric alcohol, i.e., the number of carbon atoms of the $R^{14}$ portion in formula (16), is 16. Thus, when the number of carbon atoms of the aliphatic monohydric alcohol comprising a monoether of glycerin and an aliphatic monohydric alcohol is approximately 16 or greater, the IOB value satisfies the condition of being within about 0.00 to 0.60.

In a diether of butylene glycol (n=4) and aliphatic monohydric alcohol represented by formula (17), the IOB is 0.33 when the total number of carbon atoms of the $R^{17}$ and $R^{18}$ portions is 2. Thus, when the number of carbon atoms of the aliphatic monohydric alcohol comprising a diether of butylene glycol (n=4) and an aliphatic monohydric alcohol represented by formula (17) is approximately 2 or greater, the IOB value satisfies the condition of being within about 0.00 to 0.60. Also, in a monoether of ethylene glycol (n=2) and aliphatic monohydric alcohol represented by formula (18), the IOB is 0.60 when the number of carbon atoms of the $R^{17}$ portion is 8. Thus, when the number of carbon atoms of the aliphatic monohydric alcohol in a monoether of ethylene glycol (n=2) and an aliphatic monohydric alcohol represented by formula (18) is approximately 8 or greater, the IOB value satisfies the condition of being within about 0.00 to 0.60.

Compound (B) may be produced by dehydrating condensation of a compound with 2-4 hydroxyl groups (B1) and a compound with 1 hydroxyl group, such as an aliphatic monohydric alcohol (B2), in the presence of an acid catalyst.

[(C) Ester of (C1) a Carboxylic Acid, Hydroxy Acid, Alkoxy Acid or Oxoacid Comprising a Chain Hydrocarbon Moiety and 2-4 Carboxyl Groups Substituting Hydrogens on the Chain Hydrocarbon Moiety and (C2) a Compound Having a Chain Hydrocarbon Moiety and 1 Hydroxyl Group Substituting a Hydrogen on the Chain Hydrocarbon Moiety]

The (C) ester of (C1) a carboxylic acid, hydroxy acid, alkoxy acid or oxoacid comprising a chain hydrocarbon moiety and 2-4 carboxyl groups substituting hydrogens on the chain hydrocarbon moiety and (C2) a compound having a chain hydrocarbon moiety and 1 hydroxyl group substituting a hydrogen on the chain hydrocarbon moiety (hereunder also referred to as "compound (C)") includes esters of a compound with 4, 3 or 2 carboxyl groups and a compound with 1 hydroxyl group, and it is not necessary for all of the carboxyl groups to be esterified so long as the IOB, melting point and water solubility are within the aforementioned ranges.

Examples of (C1) a carboxylic acid, hydroxy acid, alkoxy acid or oxoacid comprising a chain hydrocarbon moiety and 2-4 carboxyl groups substituting hydrogens on the chain hydrocarbon moiety (hereunder also referred to as "compound (C1)") include chain hydrocarbons hydrocarbon carboxylic acids with 2-4 carboxyl groups, such as chain hydrocarbon dicarboxylic acids including alkanedicarboxylic acids such as ethanedioic acid, propanedioic acid, butanedioic acid, pentanedioic acid, hexanedioic acid, heptanedioic acid, octanedioic acid, nonanedioic acid and decanedioic acid, chain hydrocarbon tricarboxylic acids, including alkanetricarboxylic acids such as propanetrioic acid, butanetrioic acid, pentanetrioic acid, hexanetrioic acid, heptanetrioic acid, octanetrioic acid, nonanetrioic acid and decanetrioic acid, and chain hydrocarbon tetracarboxylic acids, including alkanetetracarboxylic acids such as butanetetraoic acid, pentanetetraoic acid, hexanetetraoic acid, heptanetetraoic acid, octanetetraoic acid, nonanetetraoic acid and decanetetraoic acid.

Compound (C1) includes chain hydrocarbon hydroxy acids with 2-4 carboxyl groups, including alkoxy acids with 2-4 carboxyl groups such as malic acid, tartaric acid, citric acid and isocitric acid, including chain hydrocarbon alkoxy acids with 2-4 carboxyl groups, such as O-acetylcitric acid, and chain hydrocarbon oxoacids with 2-4 carboxyl groups.

Compounds (C2) having a chain hydrocarbon moiety and 1 hydroxyl group substituting a hydrogen on the chain hydrocarbon moiety include those mentioned for "compound (B)", such as aliphatic monohydric alcohols.

Compound (C) may be ($c_1$) an ester, for example a monoester, diester, triester or tetraester, preferably a diester, triester or tetraester, more preferably a triester or tetraester and even more preferably a tetraester, of a chain hydrocarbon tetracarboxylic acid, hydroxy acid, alkoxy acid or oxoacid with 4 carboxyl groups, and at least one aliphatic monohydric alcohol, ($c_2$) an ester, for example, a monoester, diester or triester, preferably a diester or triester and more preferably a triester, of a chain hydrocarbon tricarboxylic acid, hydroxy acid, alkoxy acid or oxoacid with 3 carboxyl groups, and at least one aliphatic monohydric alcohol, or ($c_3$) an ester, for example, a monoester or diester, and preferably a diester, of a chain hydrocarbon dicarboxylic acid, hydroxy acid, alkoxy acid or oxoacid with 2 carboxyl groups, and at least one aliphatic monohydric alcohol.

Examples for compound (C) include dioctyl adipate and tributyl O-acetylcitrate, of which commercially available products exist.

[(D) Compound Having a Chain Hydrocarbon Moiety and One Bond Selected from the Group Consisting of an Ether Bond (—O—), Carbonyl Bond (—CO—), Ester Bond (—COO—) and Carbonate Bond (—OCOO—) Inserted in a Chain Hydrocarbon Moiety and One Bond Selected from the Group Consisting of an Ether Bond (—O—), Carbonyl Bond (—CO—), Ester Bond (—COO—) and Carbonate Bond (—OCOO—) Inserted Between a C—C Single Bond of the Chain Hydrocarbon Moiety]

The (D) compound having a chain hydrocarbon moiety and one bond selected from the group consisting of an ether bond (—O—), carbonyl bond (—CO—), ester bond (—COO—) and carbonate bond (—OCOO—) inserted in-between a C—C single bond of the chain hydrocarbon moiety (hereunder also referred to as "compound (D)") may be ($d_1$) an ether of an aliphatic monohydric alcohol and an aliphatic monohydric alcohol, (d$_2$) a dialkyl ketone, (d$_3$) an ester of a fatty acid and an aliphatic monohydric alcohol, or (d$_4$) a dialkyl carbonate.

[(d$_1$) Ether of an Aliphatic Monohydric Alcohol and an Aliphatic Monohydric Alcohol]

Ethers of aliphatic monohydric alcohols and aliphatic monohydric alcohols include compounds having the following formula (19):

$$R^{19}OR^{20} \qquad (19)$$

wherein $R^{19}$ and $R^{20}$ each represent a chain hydrocarbon.

The aliphatic monohydric alcohol composing the ether (corresponding to $R^{19}OH$ and $R^{20}OH$ in formula (19)) is not particularly restricted so long as the ether satisfies the conditions for the IOB, melting point and water solubility, and for example, it may be one of the aliphatic monohydric alcohols mentioned for "compound (B)".

In an ether of an aliphatic monohydric alcohol and an aliphatic monohydric alcohol, the IOB is 0.50 when the total number of carbon atoms of the aliphatic monohydric alcohols composing the ether, i.e., the total number of carbons of the $R^{19}$ and $R^{20}$ portions in formula (19), is 2, and therefore when the total number of carbons of the aliphatic monohydric alcohols comprising the ether is about 2 or greater, this condition for the IOB is satisfied. However, when the total number of carbons of the aliphatic monohydric alcohols comprising the ether is about 6, the water solubility is as high as about 2 g, which is problematic from the viewpoint of vapor pressure as well. In order to satisfy the condition of a water solubility of about 0.00-0.05 g, the total number of carbons of the aliphatic monohydric alcohols comprising the ether is preferably about 8 or greater.

[(d$_2$) Dialkyl Ketone]

The dialkyl ketone may be a compound of the following formula (20):

$$R^{21}COR^{22} \qquad (20)$$

wherein $R^{21}$ and $R^{22}$ are each an alkyl group.

In a dialkyl ketone, the IOB is 0.54 when the total number of carbon atoms of $R^{21}$ and $R^{22}$ is 5, and therefore this condition for the IOB is satisfied if the total number of carbons is about 5 or greater. However, when the total number of carbons of dialkyl ketone is about 5, the water solubility is as high as about 2 g. Therefore, in order to satisfy the condition of a water solubility of about 0.00-0.05 g, the total number of carbons of dialkyl ketone is preferably about 8 or greater. In consideration of vapor pressure, the number of carbon atoms of dialkyl ketone is preferably about 10 or greater and more preferably about 12 or greater.

If the total number of carbon atoms of alkyl ketone is about 8, such as in 5-nonanone, for example, the melting point is approximately −50° C. and the vapor pressure is about 230 Pa at 20° C.

The dialkyl ketone may be a commercially available product, or it may be obtained by a known method, such as by oxidation of a secondary alcohol with chromic acid or the like.

[(d$_3$) Ester of a Fatty Acid and an Aliphatic Monohydric Alcohol]

Examples of esters of fatty acids and aliphatic monohydric alcohols include compounds having the following formula (21):

$$R^{23}COOR^{24} \qquad (21)$$

wherein $R^{23}$ and $R^{24}$ each represent a chain hydrocarbon.

Examples of fatty acids composing these esters (corresponding to $R^{23}COOH$ in formula (21)) include the fatty acids mentioned for the "(a$_1$) an ester of a chain hydrocarbon tetraol and at least one fatty acids", and specifically these include saturated fatty acids and unsaturated fatty acids, with saturated fatty acids being preferred in consideration of the potential for degradation by oxidation and the like. The aliphatic monohydric alcohol composing the ester (corresponding to $R^{24}OH$ in formula (21)) may be one of the aliphatic monohydric alcohols mentioned for "compound (B)".

In an ester of such a fatty acid and aliphatic monohydric alcohol, the IOB is 0.60 when the total number of carbon atoms of the fatty acid and aliphatic monohydric alcohol, i.e., the total number of carbon atoms of the $R^{23}C$ and $R^{24}$ portion in formula (21), is 5, and therefore this condition for the IOB is satisfied when the total number of carbon atoms of the $R^{23}C$ and $R^{24}$ portion is about 5 or greater. However, with butyl acetate in which the total number of carbon atoms is 6, the vapor pressure is high at greater than 2000 Pa. In consideration of vapor pressure, therefore, the total number of carbon atoms is preferably about 12 or greater. If the total number of carbon atoms is about 11 or greater, it will be possible to satisfy the condition of a water solubility of about 0.00-0.05 g.

Examples of esters of such fatty acids and aliphatic monohydric alcohols include esters of dodecanoic acid (C$_{12}$) and dodecyl alcohol (C$_{12}$) and esters of tetradecanoic acid (C$_{14}$) and dodecyl alcohol (C$_{12}$), and examples of commercial products of esters of such fatty acids and aliphatic monohydric alcohols include ELECTOL WE20 and ELECTOL WE40 (both products of NOF Corp.).

[(d$_4$) Dialkyl Carbonate]

The dialkyl carbonate may be a compound of the following formula (22):

$$R^{25}OC(=O)OR^{26} \qquad (22)$$

wherein $R^{25}$ and $R^{26}$ are each an alkyl group.

In a dialkyl carbonate, the IOB is 0.57 when the total number of carbon atoms of $R^{25}$ and $R^{26}$ is 6, and therefore this condition for the IOB is satisfied if the total number of carbons of $R^{25}$ and $R^{26}$ is about 6 or greater.

In consideration of water solubility, the total number of carbon atoms of $R^{25}$ and $R^{26}$ is preferably about 7 or greater and more preferably about 9 or greater.

The dialkyl carbonate may be a commercially available product, or it may be synthesized by reaction between phosgene and an alcohol, reaction between formic chloride and an alcohol or alcoholate, or reaction between silver carbonate and an alkyl iodide.

[(E) Polyoxy C$_2$-C$_6$ Alkylene Glycol, or Alkyl Ester or Alkyl Ether Thereof]

The (E) polyoxy C$_2$-C$_6$ alkylene glycol, or alkyl ester or alkyl ether thereof (hereunder also referred to as "compound (E)") may be (e$_1$) a polyoxy C$_2$-C$_6$ alkylene glycol, (e$_2$) an ester of a polyoxy C$_2$-C$_6$ alkylene glycol and at least one fatty acid, (e$_3$) an ether of a polyoxy C$_2$-C$_6$ alkylene glycol and at least one aliphatic monohydric alcohol, (e$_4$) an ester of polyoxy C$_2$-C$_6$ alkylene glycol and a chain hydrocarbon tetracarboxylic acid, chain hydrocarbon tricarboxylic acid or chain hydrocarbon dicarboxylic acid, or (e$_5$) an ether of polyoxy C$_2$-C$_6$ alkylene glycol and chain hydrocarbon tetraol, chain hydrocarbon triol or chain hydrocarbon diol. These will now be explained.

[(e$_1$) Polyoxy C$_2$-C$_6$ Alkylene Glycol]

The polyoxy C$_2$-C$_6$ alkylene glycol is i) a homopolymer having one backbone selected from the group consisting of polyoxy C$_2$-C$_6$ alkylene backbones, i.e., oxyethylene backbone, oxypropylene backbone, oxybutylene backbone, oxypentylene backbone and oxyhexylene backbone, and having hydroxy groups at both ends, ii) a block copolymer having a backbone of 2 or more selected from among the aforementioned group and having hydroxy groups at both ends, or iii) a random copolymer having a backbone of two or more selected from among the aforementioned group and having hydroxy groups at both ends.

The polyoxy $C_2$-$C_6$ alkylene backbone is preferably an oxypropylene backbone, oxybutylene backbone, oxypentylene backbone or oxyhexylene backbone and more preferably an oxybutylene backbone, oxypentylene backbone or oxyhexylene backbone, from the viewpoint of lowering the IOB of the polyoxy $C_2$-$C_6$ alkylene glycol.

When polyoxy $C_2$-$C_6$ alkylene glycol is a homopolymer, the poly $C_{3-6}$ alkylene glycol is represented by the following formula (23):

$$HO\text{—}(C_mH_{2m}O)_n\text{—}H \quad (23)$$

wherein m is an integer of 3-6.

The present inventors have confirmed that in polyethylene glycol (corresponding to formula (23) where m=2), when n≥45 (the molecular weight exceeds about 2,000), the condition for IOB of about 0.00 to about 0.60 is satisfied, but the condition for the water solubility is not satisfied even when the molecular weight exceeds 4,000. Therefore, ethylene glycol homopolymer is not included in the ($e_1$) polyoxy $C_2$-$C_6$ alkylene glycol, and ethylene glycol should be included in the ($e_1$) polyoxy $C_2$-$C_6$ alkylene glycol only as a copolymer or random polymer with another glycol.

Thus, homopolymers of formula (23) may include propylene glycol, butylene glycol, pentylene glycol or hexylene glycol homopolymer.

For this reason, m in formula (23) is about 3 to 6 and preferably about 4 to 6, and n is 2 or greater.

The value of n in formula (23) is a value such that the polyoxy $C_2$-$C_6$ alkylene glycol has an IOB of about 0.00-0.60, a melting point of no higher than about 45° C. and a water solubility of no greater than about 0.05 g in 100 g of water at 25° C.

For example, when formula (23) is polypropylene glycol (m=3), the IOB is 0.58 when n=12. Thus, when formula (23) is polypropylene glycol (m=3), the condition for the IOB is satisfied when n is equal to or greater than about 12.

Also, when formula (23) is polybutylene glycol (m=4), the IOB is 0.57 when n=7. Thus, when formula (23) is polybutylene glycol (m=4), the condition for the IOB is satisfied when n is equal to or greater than about 7.

From the viewpoint of IOB, melting point and water solubility, the weight-average molecular weight of the polyoxy $C_2$-$C_6$ alkylene glycol is preferably between about 200 and about 10,000, more preferably between about 250 and about 8,000, and even more preferably in the range of about 250 to about 5,000.

Also from the viewpoint of IOB, melting point and water solubility, the weight-average molecular weight of a poly $C_3$ alkylene glycol, i.e., polypropylene glycol, is preferably between about 1,000 and about 10,000, more preferably between about 3,000 and about 8,000, and even more preferably between about 4,000 and about 5,000. This is because if the weight-average molecular weight is less than about 1,000, the condition for the water solubility will not be satisfied, and a larger weight-average molecular weight will particularly tend to increase the migration rate into the absorbent body and the whiteness of the top sheet.

Examples of commercial products of polyoxy $C_2$-$C_6$ alkylene glycols include UNIOL™ D-1000, D1200, D-2000, D-3000, D-4000, PB-500, PB-700, PB-1000 and PB-2000 (both products of NOF Corp.).

[($e_2$) Ester of Polyoxy $C_2$-$C_6$ Alkylene Glycol and at Least One Fatty Acid]

Esters of such polyoxy $C_2$-$C_6$ alkylene glycols and at least one fatty acid include the polyoxy $C_2$-$C_6$ alkylene glycols mentioned for "($e_1$) Polyoxy $C_2$-$C_6$ alkylene glycol" in which one or both OH ends have been esterified with fatty acids, i.e., monoesters and diesters.

Examples of fatty acids to be esterified in the ester of a polyoxy $C_2$-$C_6$ alkylene glycol and at least one fatty acid include the fatty acids mentioned for the "($a_1$) Esters of chain hydrocarbon tetraols and at least one fatty acid", and specifically these include saturated fatty acids and unsaturated fatty acids, with saturated fatty acids being preferred in consideration of the potential for degradation by oxidation and the like. An example of a commercially available ester of a polyoxy $C_2$-$C_6$ alkylene glycol a fatty acid is WILLBRITE cp9 (product of NOF Corp.).

[($e_3$) Ether of Polyoxy $C_2$-$C_6$ Alkylene Glycol and at Least One Aliphatic Monohydric Alcohol]

Ethers of such polyoxy $C_2$-$C_6$ alkylene glycols and at least one aliphatic monohydric alcohol include the polyoxy $C_2$-$C_6$ alkylene glycols mentioned for "($e_1$) polyoxy $C_2$-$C_6$ alkylene glycol" wherein one or both OH ends have been etherified by an aliphatic monohydric alcohol, i.e., monoethers and diethers.

In an ether of a polyoxy $C_2$-$C_6$ alkylene glycol and at least one aliphatic monohydric alcohol, the aliphatic monohydric alcohol to be etherified may be an aliphatic monohydric alcohol among those mentioned for "compound (B)".

[($e_4$) Ester of Polyoxy $C_2$-$C_6$ Alkylene Glycol and Chain Hydrocarbon Tetracarboxylic Acid, Chain Hydrocarbon Tricarboxylic Acid or Chain Hydrocarbon Dicarboxylic Acid]

The polyoxy $C_2$-$C_6$ alkylene glycol to be esterified for the aforementioned ester of a polyoxy $C_2$-$C_6$ alkylene glycol and a chain hydrocarbon tetracarboxylic acid, chain hydrocarbon tricarboxylic acid or chain hydrocarbon dicarboxylic acid may be any of the polyoxy $C_2$-$C_6$ alkylene glycols mentioned above under "($e_1$) Polyoxy $C_2$-$C_6$ alkylene glycol". Also, the chain hydrocarbon tetracarboxylic acid, chain hydrocarbon tricarboxylic acid or chain hydrocarbon dicarboxylic acid to be esterified may be any of those mentioned above for "compound (C)".

The ester of a polyoxy $C_2$-$C_6$ alkylene glycol and a chain hydrocarbon tetracarboxylic acid, chain hydrocarbon tricarboxylic acid or chain hydrocarbon dicarboxylic acid may be a commercially available product, or it may be produced by polycondensation of a polyoxy $C_2$-$C_6$ alkylene glycol with a chain hydrocarbon tetracarboxylic acid, chain hydrocarbon tricarboxylic acid or chain hydrocarbon dicarboxylic acid under known conditions.

[($e_5$) Ether of Polyoxy $C_2$-$C_6$ Alkylene Glycol and Chain Hydrocarbon Tetraol, Chain Hydrocarbon Triol or Chain Hydrocarbon Diol]

The polyoxy $C_2$-$C_6$ alkylene glycol to be etherified for the aforementioned ether of a polyoxy $C_2$-$C_6$ alkylene glycol and a chain hydrocarbon tetraol, chain hydrocarbon triol or chain hydrocarbon diol may be any of the polyoxy $C_2$-$C_6$ alkylene glycols mentioned above under "($e_1$) Polyoxy $C_2$-$C_6$ alkylene glycol". Also, the chain hydrocarbon tetraol, chain hydrocarbon triol or chain hydrocarbon diol to be etherified may be, for example, pentaerythritol, glycerin or glycol, mentioned above for "compound (A)".

Examples of commercially available ethers of polyoxy $C_2$-$C_6$ alkylene glycols and chain hydrocarbon tetraols, chain hydrocarbon triols and chain hydrocarbon diols include UNILUBE™ 5TP-300KB and UNIOL™ TG-3000 and TG-4000 (products of NOF Corp.).

UNILUBE™ 5TP-300KB is a compound obtained by polycondensation of 65 mol of propylene glycol and 5 mol of ethylene glycol with 1 mol of pentaerythritol, and it has an IOB of 0.39, a melting point of below 45° C., and a water solubility of less than 0.05 g.

UNIOL™ TG-3000 is a compound obtained by polycondensation of 50 mol of propylene glycol with 1 mol of glycerin, and it has an IOB of 0.42, a melting point of below 45° C., a water solubility of less than 0.05 g, and a weight-average molecular weight of about 3,000.

UNIOL™ TG-4000 is a compound obtained by polycondensation of 70 mol of propylene glycol with 1 mol of glycerin, and it has an IOB of 0.40, a melting point of below 45° C., a water solubility of less than 0.05 g, and a weight-average molecular weight of about 4,000.

The ether of a poly $C_2$-$C_6$ alkylene glycol and a chain hydrocarbon tetraol, chain hydrocarbon triol or chain hydrocarbon diol may also be produced by polycondensation of a polyoxy $C_2$-$C_6$ alkylene glycol with a chain hydrocarbon tetraol, chain hydrocarbon triol or chain hydrocarbon diol under known conditions.

[(F) Chain Hydrocarbon]

The chain hydrocarbon has an inorganic value of 0 and thus an IOB of 0.00, while the water solubility is also approximately 0 g, and therefore if the melting point is no higher than about 45° C., it may be included among the aforementioned blood modifying agents. Examples of such chain hydrocarbons include ($f_1$) chain alkanes, such as linear alkanes and branched alkanes, and linear alkanes generally include those with no more than 22 carbons, in consideration of a melting point of no higher than about 45° C. In consideration of vapor pressure, they generally include those with 13 or more carbons. Branched alkanes generally include those with 22 or more carbons, since their melting points are often lower than linear alkanes, given the same number of carbon atoms.

Examples of commercially available hydrocarbon products include PARLEAM 6 (NOF Corp.).

The blood modifying agent has been found to exhibit at least action of lowering blood viscosity and surface tension, which will be considered in detail in the examples. Menstrual blood to be absorbed by the absorbent article, unlike ordinary blood, contains proteins of the endometrial wall, for example, which act to bind together blood cells so that the blood cells form a rouleau state. Menstrual blood which is to be absorbed by the absorbent article therefore tends to have high viscosity, and when the top sheet is a nonwoven fabric or woven fabric, the menstrual blood becomes clogged between the fibers creating a residual sticky feel for the wearer, while the menstrual blood also diffuses on the surface of the top sheet and tends to leak.

In addition, the blood modifying agent which has an IOB of about 0.00 to 0.60 has high organicity and readily infiltrates between blood cells, and it therefore stabilizes the blood cells and can prevent formation of a rouleau structure by the blood cells. It is believed that, since the modifier stabilizes blood cells and helps to prevent formation of a rouleau structure by the blood cells, it facilitates absorption of menstrual blood by the absorbent body. For example, with an absorbent article comprising an acrylic super-absorbent polymer, or SAP, absorption of menstrual blood is known to lead to covering of the SAP surface by rouleau-formed blood cells and inhibition of the absorption performance of the SAP, but presumably stabilization of the blood cells allows the absorption performance of the SAP to be exhibited more easily. In addition, the blood modifying agent which has high affinity with erythrocytes protects the erythrocyte membranes, and therefore may minimize destruction of the erythrocytes.

Figure 4:
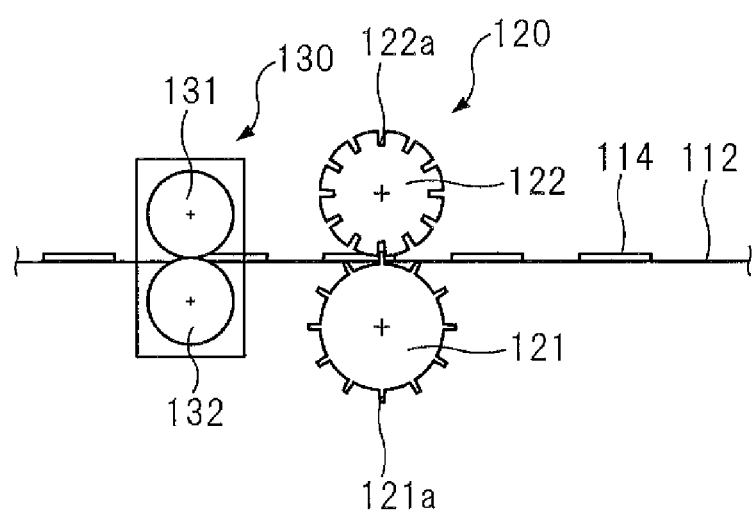
FIG. 4 is a diagram illustrating an example of a method of forming openings in a top sheet and absorbent body.

A method of forming the openings 10 in the top sheet 2 and absorbent body 4 will now be described. FIG. 4 is a diagram illustrating an example of a method of forming openings 10 in a top sheet 2 and absorbent body 4.

The absorbent body 114 having its outer side covered with a wrap sheet is placed on a top sheet 112 supplied from a top sheet roll (not shown).

Next, a through-hole forming apparatus 120 is used to form openings in the top sheet 112 and absorbent body 114, running through them in the thickness direction. The through-hole forming apparatus 120 comprises a protrusion roll 121 having a plurality of needle-like, circular cylindrical or conical shaped protrusions 121a on the outer peripheral surface, and an anvil roll 122 having recesses 122a on the outer peripheral surface which engages with the protrusions 121a, at locations corresponding to the protrusions 121a of the protrusion roll 121.

As the protrusions 121a of the protrusion roll 121 penetrate the front sheet 112 and absorbent body 114, openings are formed in the front sheet 112 and absorbent body 114. The rotational speeds of the protrusion roll 121 and anvil roll 122 are adjusted so that holes are opened in the wrap sheet covering the absorbent body, after the wrap sheet has been stretched. This allows openings, where the opening interiors of the absorbent body are covered by the wrap sheet, to be formed in the absorbent body 114. At this stage, the top sheet 112 is not yet detached from the absorbent body 114.

Next, an embossing apparatus 130 is used to form compressed grooves in the top sheet 112 and absorbent body 114. The top sheet 112 and absorbent body 114 in which openings have been formed are passed between the upper roll 131 and lower roll 132 of the embossing apparatus 130. The upper roll 131 is a plain roll having a smooth outer peripheral surface. Heights (not shown) with shapes corresponding to the compressed grooves 11 of the absorbent article 1 shown in FIG. 1 are provided on the outer peripheral surface of the lower roll 132. When the layered body 262 passes between the upper roll 131 and lower roll 132 of the embossing apparatus 130, the top sheet 112 and absorbent body 114 are compressed in the thickness direction, and compressed grooves are formed in the top sheet 112 and absorbent body 114. When the compressed grooves are formed in the top sheet 112 and absorbent body 114, the top sheet 112 becomes detached from the absorbent body 114 at the openings.

This is followed by a step of providing a side sheet, a step of providing a back sheet, a step of forming a seal section, a step of punching into the outer shape of absorbent article, and a step of coating a blood modifying agent, described hereunder, to produce an absorbent article from the top sheet 112 and absorbent body 114.

The absorbent article according to the embodiment described above may incorporate the following modifications.

Figure 5:
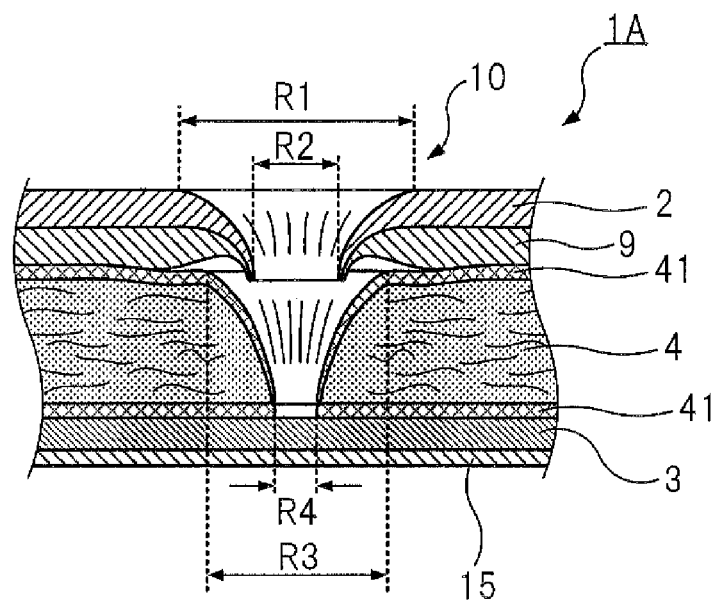
FIG. 5 is a simplified cross-sectional view of an opening in a modified example of an absorbent article according to an embodiment of the invention.

(1) As shown in FIG. 5, the absorbent article 1A may comprise a second sheet 9 between the top sheet 2 and absorbent body 4. FIG. 5 is a simplified cross-sectional view of an opening in a modified example of an absorbent article according to an embodiment of the invention. The second sheet 9 is used to speed absorption of menstrual blood from the skin side of the absorbent body 4 by causing menstrual blood of the wearer that has been excreted into the top sheet 2 to diffuse in the planar direction, and to increase the cushioning property of the absorbent article 1A. The second sheet 9 may employ a hydrophilic liquid-permeable material such as a woven fabric, nonwoven fabric, porous plastic, fluff pulp or the like.

The second sheet 9 is preferably bonded to the top sheet 2 using an adhesive such as a hot-melt adhesive. This will allow body fluid of the wearer to be rapidly absorbed by the top sheet 2 and migrate into the absorbent body 4. A material with a higher basis weight and higher density than the top sheet 2 may be used in the second sheet 9. This can increase the rate of migration of body fluid from the top sheet 2 into the second sheet 9.

The second sheet 9 has openings 10 provided at locations in the thickness direction corresponding to the openings 10 of the top sheet 2. At the openings 10, the second sheet 9 is detached from the absorbent body 4. Also, the opening diameter R1 of the openings 10 on the skin side of the top sheet 2 is larger than the opening diameter R2 of the openings 10 on the clothing side of the second sheet 9, the opening diameter R2 of the openings 10 on the clothing side of the second sheet 9 is smaller than the opening diameter R3 of the openings 10 on the skin side of the absorbent body 4, and the opening diameter R4 of the openings 10 on the clothing side of the absorbent body 4 is no greater than the size of the opening diameter R2 of the openings 10 on the clothing side of the second sheet 9. In this case as well, the opening diameter R1 of the openings 10 on the skin side of the top sheet 2 is smaller than the opening diameter R3 of the openings 10 on the clothing side of the absorbent body 4.

(2) In the embodiments described above, the openings 10 in the absorbent body 4 were through-holes, but they may be non-through-holes instead. In such cases, the value of the opening diameter R4 of the openings on the clothing side of the absorbent body 4 (see FIG. 2(b)) will be 0.

Any of the aforementioned embodiments may also be applied in combination with the modifications. The modifications may also be applied in combination with each other.

The explanation above is merely an example, and the invention is in no way restricted by the described embodiment.

EXAMPLES

By the following examples it was confirmed that the blood modifying agent lowers the viscosity and surface tension of menstrual blood and allows menstrual blood to rapidly migrate from the top sheet 2 into the absorbent body 4. The invention will now be explained by examples, with the understanding that the invention is not meant to be limited to the examples.

Example 1

Evaluation of Rewetting Rate and Absorbent Body Migration Rate

[Data of Blood Modifying Agents]

A commercially available sanitary napkin was prepared. The sanitary napkin was formed from a top sheet, formed of a hydrophilic agent-treated air-through nonwoven fabric (composite fiber composed of polyester and polyethylene terephthalate, basis weight: 35 g/m$^2$), a second sheet, formed of an air-through nonwoven fabric (composite fiber composed of polyester and polyethylene terephthalate, basis weight: 30 g/m$^2$), an absorbent body comprising pulp (basis weight: 150-450 g/m$^2$, increased at the center section), an acrylic super-absorbent polymer (basis weight: 15 g/m$^2$) and tissue as a core wrap, a water-repellent agent-treated side sheet, and a back sheet composed of a polyethylene film.

The blood modifying agents used for the experiment are listed below.

[($a_1$) Ester of a Chain Hydrocarbon Tetraol and at Least One Fatty Acid]

UNISTAR H-408BRS, product of NOF Corp.
Tetrapentaerythritol 2-ethylhexanoate, weight-average molecular weight: approximately 640

UNISTAR H-2408BRS-22, product of NOF Corp.
Mixture of tetrapentaerythritol 2-ethylhexanoate and di-neopentyl 2-ethylhexanoate glycol (58:42, mass ratio), weight-average molecular weight: approximately 520

[($a_2$) Ester of a Chain Hydrocarbon Triol and at Least One Fatty Acid]

Cetiol SB45DEO, Cognis Japan
Glycerin and fatty acid triester, with oleic acid or stearylic acid as the fatty acid.

SOY42, product of NOF Corp.
Glycerin and fatty acid triester with $C_{14}$ fatty acid:$C_{16}$ fatty acid:$C_{18}$ fatty acid:$C_{20}$ fatty acid (including both saturated fatty acids and unsaturated fatty acids) at a mass ratio of about 0.2:11:88:0.8, weight-average molecular weight: 880

Tri-C2L oil fatty acid glyceride, product of NOF Corp.
Glycerin and fatty acid triester with $C_8$ fatty acid:$C_{10}$ fatty acid:$C_{12}$ fatty acid at a mass ratio of about 37:7:56, weight-average molecular weight: approximately 570

Tri-CL oil fatty acid glyceride, product of NOF Corp.
Glycerin and fatty acid triester with $C_8$ fatty acid:$C_{12}$ fatty acid at a mass ratio of about 44:56, weight-average molecular weight: approximately 570

PANACET 810s, product of NOF Corp.
Glycerin and fatty acid triester with $C_8$ fatty acid:$C_{10}$ fatty acid at a mass ratio of about 85:15, weight-average molecular weight: approximately 480

PANACET 800, product of NOF Corp.
Glycerin and fatty acid triester with octanoic acid ($C_8$) as the entire fatty acid portion, weight-average molecular weight: approximately 470

PANACET 800B, product of NOF Corp.
Glycerin and fatty acid triester with 2-ethylhexanoic acid ($C_8$) as the entire fatty acid portion, weight-average molecular weight: approximately 470

NA36, product of NOF Corp.
Glycerin and fatty acid triester with $C_{16}$ fatty acid:$C_{18}$ fatty acid:$C_{20}$ fatty acid (including both saturated fatty acids and unsaturated fatty acids) at a mass ratio of about 5:92:3, weight-average molecular weight: approximately 880

Tri-coconut fatty acid glyceride, product of NOF Corp.
Glycerin and fatty acid triester with $C_8$ fatty acid:$C_{10}$ fatty acid:$C_{12}$ fatty acid:$C_{14}$ fatty acid:$C_{16}$ fatty acid (including both saturated fatty acids and unsaturated fatty acids) at a mass ratio of about 4:8:60:25:3, weight-average molecular weight: 670

Caprylic acid diglyceride, product of NOF Corp.
Glycerin and fatty acid diester with octanoic acid as the fatty acid, weight-average molecular weight: approximately 340

[($a_3$) Ester of a Chain Hydrocarbon Diol and at Least One Fatty Acid]

COMPOL BL, product of NOF Corp.
Dodecanoic acid ($C_{12}$) monoester of butylene glycol, weight-average molecular weight: approximately 270

COMPOL BS, product of NOF Corp.
Octadecanoic acid ($C_{18}$) monoester of butylene glycol, weight-average molecular weight: approximately 350

UNISTAR H-208BRS, product of NOF Corp.
Neopentylglycol di-2-ethylhexanoate, weight-average molecular weight: approximately 360.

[(c₂) Ester of a Chain Hydrocarbon Tricarboxylic Acid, Hydroxy Acid, Alkoxy Acid or Oxoacid with 3 Carboxyl Groups, and at Least One Aliphatic Monohydric Alcohol]
Tributyl O-acetylcitrate, product of Tokyo Kasei Kogyo Co., Ltd.
  Weight-average molecular weight: approximately 400
[(c₃) Ester of a Chain Hydrocarbon Dicarboxylic Acid, Hydroxy Acid, Alkoxy Acid or Oxoacid with 2 Carboxyl Groups, and at Least One Aliphatic Monohydric Alcohol]
Dioctyl adipate, product of Wako Pure Chemical Industries, Ltd.
  Weight-average molecular weight: approximately 380
[(d₃) Ester of a Fatty Acid and an Aliphatic Monohydric Alcohol]
ELECTOL WE20, product of NOF Corp.
  Ester of dodecanoic acid ($C_{12}$) and dodecyl alcohol ($C_{12}$), weight-average molecular weight: approximately 360
ELECTOL WE40, product of NOF Corp.
  Ester of tetradecanoic acid ($C_{14}$) and dodecyl alcohol ($C_{12}$), weight-average molecular weight: approximately 390
[(e₁) Polyoxy $C_2$-$C_6$ Alkylene Glycol]
UNIOL D-1000, product of NOF Corp.
  Polypropylene glycol, weight-average molecular weight: approximately 1,000
UNIOL D-1200, product of NOF Corp.
  Polypropylene glycol, weight-average molecular weight: approximately 1,160
UNIOL D-3000, product of NOF Corp.
  Polypropylene glycol, weight-average molecular weight: approximately 3,000
UNIOL D-4000, product of NOF Corp.
  Polypropylene glycol, weight-average molecular weight: approximately 4,000
UNIOL PB500, product of NOF Corp.
  Polybutylene glycol, weight-average molecular weight: approximately 500
UNIOL PB700, product of NOF Corp.
  Polyoxybutylenepolyoxypropylene glycol, weight-average molecular weight: approximately 700
UNIOL PB1000R, product of NOF Corp.
  Polybutylene glycol, weight-average molecular weight: approximately 1,000
[(e₂) Ester of a Polyoxy $C_2$-$C_6$ Alkylene Glycol and at Least One Fatty Acid]
WILBRITE cp9, product of NOF Corp.
  Polybutylene glycol compound with OH groups at both ends esterified by hexadecanoic acid ($C_{16}$), weight-average molecular weight: approximately 1,150
[(e₃) Ether of Polyoxy $C_2$-$C_6$ Alkylene Glycol and at Least One Fatty Acid]
UNILUBE MS-70K, product of NOF Corp.
  Stearyl ether of polypropylene glycol, approximately 15 repeating units, weight-average molecular weight: approximately 1,140
[(e₅) Ether of a Polyoxy $C_2$-$C_6$ Alkylene Glycol with Chain Hydrocarbon Tetraol, Chain Hydrocarbon Triol or Chain Hydrocarbon Diol]
UNILUBE 5TP-300KB
  Polyoxyethylenepolyoxypropylene pentaerythritol ether, produced by addition of 5 mol of ethylene oxide and 65 mol of propylene oxide to 1 mol of pentaerythritol, weight-average molecular weight: 4,130
UNIOL TG-3000, product of NOF Corp.
  Glyceryl ether of polypropylene glycol, approximately 16 repeating units, weight-average molecular weight: approximately 3,000
UNIOL TG-4000, product of NOF Corp.
  Glyceryl ether of polypropylene glycol, approximately 16 repeating units, weight-average molecular weight: approximately 4,000
[(f₁) Chain Alkane]
PARLEAM 6, product of NOF Corp.
  Branched hydrocarbon, produced by copolymerization of liquid isoparaffin, isobutene and n-butene followed by hydrogen addition, polymerization degree: approximately 5-10, weight-average molecular weight: approximately 330
[Other Components]
NA50, product of NOF Corp.
  Glycerin and fatty acid triester obtained by addition of hydrogen to NA36 for reduced proportion of double bonds from unsaturated fatty acid starting material, weight-average molecular weight: approximately 880
(Caprylic acid/capric acid) monoglyceride, product of NOF Corp.
  Glycerin and fatty acid monoester, with octanoic acid ($C_8$) and decanoic acid ($C_{10}$) at a mass ratio of about 85:15, weight-average molecular weight: approximately 220
Monomuls 90-L2 lauric acid monoglyceride, product of Cognis Japan
Isopropyl citrate, product of Tokyo Kasei Kogyo Co., Ltd.
  Weight-average molecular weight: approximately 230
Diisostearyl malate
  Weight-average molecular weight: approximately 640
UNIOL D-400, product of NOF Corp.
  Polypropylene glycol, weight-average molecular weight: approximately 400
PEG1500, product of NOF Corp.
  Polyethylene glycol, weight-average molecular weight: approximately 1,500-1,600
NONION S-6, product of NOF Corp.
  Polyoxyethylene monostearate, approximately 7 repeating units, weight-average molecular weight: approximately 880
WILBRITE s753, product of NOF Corp.
  Polyoxyethylenepolyoxypropylene polyoxybutylene glycerin, weight-average molecular weight: approximately 960
UNIOL TG-330, product of NOF Corp.
  Glyceryl ether of polypropylene glycol, approximately 6 repeating units, weight-average molecular weight: approximately 330
UNIOL TG-1000, product of NOF Corp.
  Glyceryl ether of polypropylene glycol, approximately 16 repeating units, weight-average molecular weight: approximately 1,000
UNILUBE DGP-700, product of NOF Corp.
  Diglyceryl ether of polypropylene glycol, approximately 9 repeating units, weight-average molecular weight: approximately 700
UNIOX HC60, product of NOF Corp.
  Polyoxyethylene hydrogenated castor oil, weight-average molecular weight: approximately 3,570
Vaseline, product of Cognis Japan
  Petroleum-derived hydrocarbon, semi-solid
  The IOBs, melting points and water solubilities of the samples are shown in Table 2.
  The water solubility was measured by the method described above, and samples that dissolved 24 hours after addition of 20.0 g to 100 g of desalted water were evaluated as "20 g<", and samples of which 0.05 g dissolved in 100 g of desalted water but 1.00 g did not dissolve were evaluated as 0.05-1.00 g.
  For the melting point, "<45" indicates a melting point of below 45° C.

The skin contact surface of the top sheet of the sanitary napkin was coated with the aforementioned blood modifying agent. Each blood modifying agent was used directly, when the blood modifying agent was liquid at room temperature, or when the blood modifying agent was solid at room temperature it was heated to its melting point of +20° C., and a control seam HMA gun was used for atomization of the blood modifying agent and coating onto the entire skin contact surface of the top sheet to a basis weight of about 5 g/m².

Figure 6:
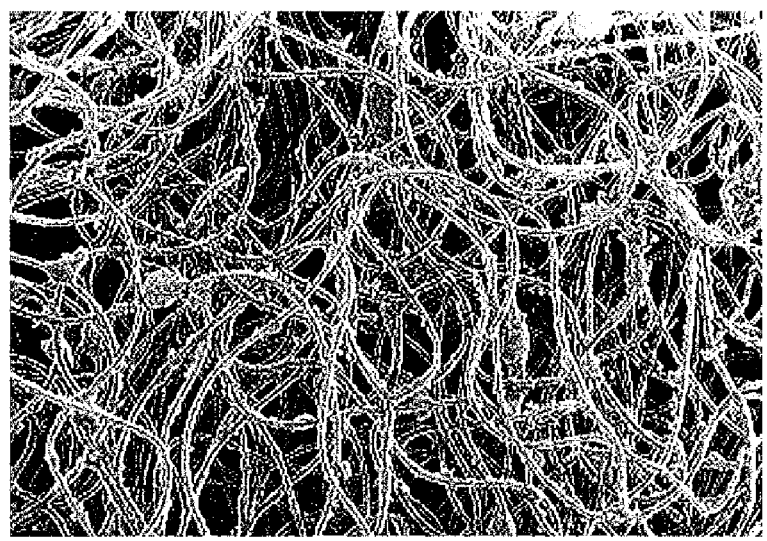
FIG. 6 is an electron micrograph of the skin contact surface of a top sheet in a sanitary napkin wherein the top sheet comprises tri-C2L oil fatty acid glycerides.

FIG. 6 is an electron micrograph of the skin contact surface of a top sheet in a sanitary napkin (No. 2-5) wherein the top sheet comprises tri-C2L oil fatty acid glycerides. As clearly seen in FIG. 6, the tri-C2L oil fatty acid glycerides are present on the fiber surfaces as fine particulates.

In accordance with the above procedures, the rewetting rate and absorber migration rate were measured. The results are shown below in Table 2.

[Test Methods]

An acrylic board with an opened hole (200 mm×100 mm, 125 g, with a 40 mm×10 mm hole opened at the center) was placed on a top sheet comprising each blood modifying agent, and 3 g of horse EDTA blood at 37±1° C. (obtained by adding appropriate amount of ethylenediaminetetraacetic acid (hereunder, "EDTA") to horse blood to prevent coagulation) was dropped through the hole using a pipette (once), and after 1 minute, 3 g of horse EDTA blood at 37±1° C. was again added dropwise through the acrylic board hole with a pipette (twice).

After the second dropping of blood, the acrylic board was immediately removed and 10 sheets of filter paper (Advantec Toyo Kaisha, Ltd, Qualitative Filter Paper No. 2, 50 mm×35 mm) were placed on the location where the blood had been dropped, and then a weight was placed thereover to a pressure of 30 g/cm². After 1 minute, the filter paper was removed and the "rewetting rate" was calculated by the following formula.

Rewetting rate (%)=100×(filter paper mass after test−initial filter paper mass)/6

In addition to the rewetting rate evaluation, the "absorbent body migration rate" was also measured as the time until migration of blood from the top sheet to the absorbent body after the second dropping of blood. The absorbent body migration rate is the time from introducing the blood onto the top sheet, until the redness of the blood could be seen on the surface and in the interior of the top sheet.

The results for the rewetting rate and absorbent body migration rate are shown below in Table 2.

Then the whiteness of the skin contact surface of the top sheet after the absorbent body migration rate test was visually evaluated on the following scale.

VG (Very Good): Virtually no redness of blood remaining, and no clear delineation between areas with and without blood.

G (Good): Slight redness of blood remaining, but difficult to delineate between areas with and without blood.

F (Fair): Slight redness of blood remaining, areas with blood discernible.

P (Poor): Redness of blood completely remaining. The results are summarized below in Table 2.

TABLE 2

| No. | Type | Blood modifying agent Product name | IOB | Melting point (° C.) | Water solubility (g) | Weight-average mol. wt. | Rewetting rate (%) | Absorber migration rate (sec) | Top sheet whiteness |
|---|---|---|---|---|---|---|---|---|---|
| 2-1 | (A₁) | UNISTAR H-408BRS | 0.13 | <−5 | <0.05 | 640 | 1.2 | 3 | VG |
| 2-2 | | UNISTAR H-2408BRS-22 | 0.18 | <−5 | <0.05 | 520 | 2.0 | 3 | VG |
| 2-3 | (A₂) | CETIOL SB45DEO | 0.16 | 44 | <0.05 | | 7.0 | 6 | VG |
| 2-4 | | SOY42 | 0.16 | 43 | <0.05 | 880 | 5.8 | 8 | VG |
| 2-5 | | Tri-C2L oil fatty acid glyceride | 0.27 | 37 | <0.05 | 570 | 0.3 | 3 | VG |
| 2-6 | | Tri-CL oil fatty acid glyceride | 0.28 | 38 | <0.05 | 570 | 1.7 | 3 | VG |
| 2-7 | | PANACET 810s | 0.32 | −5 | <0.05 | 480 | 2.8 | 3 | VG |
| 2-8 | | PANACET 800 | 0.33 | −5 | <0.05 | 470 | 0.3 | 3 | VG |
| 2-9 | | PANACET 800B | 0.33 | −5 | <0.05 | 470 | 2.0 | 3 | VG |
| 2-10 | | NA36 | 0.16 | 37 | <0.05 | 880 | 3.9 | 5 | VG |
| 2-11 | | Tri-coconut fatty acid glyceride | 0.28 | 30 | <0.05 | 670 | 4.3 | 5 | VG |
| 2-12 | | Caprylic acid diglyceride | 0.58 | <45 | <0.05 | 340 | 4.2 | 9 | G |
| 2-13 | (A₃) | COMPOL BL | 0.50 | 2 | <0.05 | 270 | 2.0 | 5 | G |
| 2-14 | | COMPOL BS | 0.36 | 37 | <0.05 | 350 | 7.9 | 9 | G |
| 2-15 | | UNISTAR H-208BRS | 0.24 | <−5 | <0.05 | 360 | 2.0 | 5 | VG |
| 2-16 | (C₂) | Tributyl O-acetylcitrate | 0.60 | <45 | <0.05 | 400 | 6.2 | 8 | VG |
| 2-17 | (C₃) | Dioctyl adipate | 0.27 | <45 | <0.05 | 380 | 1.7 | 6 | VG |
| 2-18 | (D₃) | ELECTOL WE20 | 0.13 | 29 | <0.05 | 360 | 1.8 | 5 | VG |
| 2-19 | | ELECTOL WE40 | 0.12 | 37 | <0.05 | 390 | 1.8 | 4 | VG |
| 2-20 | (E₁) | UNIOL D-1000 | 0.51 | <45 | <0.05 | 1,000 | 6.8 | 15 | F |
| 2-21 | | UNIOL D-1200 | 0.48 | <45 | <0.05 | 1,160 | 0.5 | 11 | F |
| 2-22 | | UNIOL D-3000 | 0.39 | <45 | <0.05 | 3,000 | 1.7 | 10 | |
| 2-23 | | UNIOL D-4000 | 0.38 | <45 | <0.05 | 4,000 | 1.0 | 7 | G |
| 2-24 | (E₁) | UNIOL PB500 | 0.44 | <45 | <0.05 | 500 | 4.5 | 4 | G |
| 2-25 | | UNIOL PB700 | 0.49 | −5 | <0.05 | 700 | 2.8 | 5 | G |
| 2-26 | | UNIOL PB1000R | 0.40 | <45 | <0.05 | 1,000 | 4.0 | 4 | G |
| 2-27 | (E₂) | WILBRITE cp9 | 0.21 | 35 | <0.05 | 1,150 | 1.4 | 3 | G |
| 2-28 | (E₃) | UNILUBE MS-70K | 0.30 | <−10 | <0.05 | 1,140 | 6.7 | 3 | G |
| 2-29 | (E₅) | UNILUBE 5TP-300KB | 0.39 | <45 | <0.05 | 4,130 | 2.0 | 6 | G |
| 2-30 | | UNIOL TG-3000 | 0.42 | <45 | <0.05 | 3,000 | 0.8 | 6 | G |
| 2-31 | | UNIOL TG-4000 | 0.40 | <45 | <0.05 | 4,000 | 2.0 | 6 | G |
| 2-32 | (F₁) | PARLEAM 6 | 0.00 | −5 | <0.05 | 330 | 6.0 | 8 | VG |
| 2-33 | | NA50 | 0.18 | 52 | <0.05 | 880 | 15.5 | 60 | P |
| 2-34 | | (Caprylic acid/capric acid) monoglyceride | 1.15 | <45 | 20< | 220 | 4.0 | 4 | P |
| 2-35 | | Monomuls 90-L2 lauric acid monoglyceride | 0.87 | 58 | 20< | | 6.2 | 7 | P |
| 2-36 | | Isopropyl citrate | 1.56 | <45 | 20< | 230 | 12.2 | 5 | G |
| 2-37 | | Diisostearyl malate | 0.28 | <45 | 20< | 640 | 5.5 | 8 | F |

TABLE 2-continued

| No. | Blood modifying agent Type | Product name | IOB | Melting point (°C.) | Water solubility (g) | Weight-average mol. wt. | Rewetting rate (%) | Absorber migration rate (sec) | Top sheet whiteness |
|---|---|---|---|---|---|---|---|---|---|
| 2-38 | | UNIOL D-400 | 0.76 | <45 | 0.05< | 400 | 8.7 | 40 | P |
| 2-39 | | PEG1500 | 0.78 | 40 | 20< | 1,500-1,600 | 11.0 | 38 | P |
| 2-40 | | NONION S-6 | 0.44 | 37 | 0.05< | 880 | 8.4 | 7 | P |
| 2-41 | | WILBRITE s753 | 0.67 | −5 | 20< | 960 | 9.3 | 9 | F |
| 2-42 | | UNIOL TG-330 | 1.27 | <45 | 0.05< | 330 | — | — | — |
| 2-43 | | UNIOL TG-1000 | 0.61 | <45 | <0.05 | 1,000 | 14.2 | 7 | G |
| 2-44 | | UNILUBE DGP-700 | 0.91 | <0 | 0.05< | 700 | 8.0 | 10 | F |
| 2-45 | | UNIOX HC60 | 0.46 | 33 | 0.05-1.00 | 3,570 | 14.6 | 46 | P |
| 2-46 | | Vaseline | 0.00 | 55 | <0.05 | | 9.7 | 10 | F |
| 2-47 | | None | — | — | — | — | 22.7 | 60< | P |

In the absence of a blood modifying agent, the rewetting rate was 22.7% and the absorbent body migration rate was greater than 60 seconds, but the glycerin and fatty acid triesters all produced rewetting rates of no greater than 7.0% and absorbent body migration rates of no longer than 8 seconds, and therefore significantly improved the absorption performance. Of the glycerin and fatty acid triesters, however, no great improvement in absorption performance was seen with NA50 which had a melting point of above 45° C.

Similarly, the absorption performance was also significantly improved with blood modifying agents having an IOB of about 0.00-0.60, a melting point of no higher than about 45° C. and a water solubility of no greater than about 0.05 g in 100 g of water at 25° C. Rewetting rates of no greater than 7.9% and absorbent body migration rates of no longer than 15 seconds were achieved.

Next, several volunteer subjects were asked to wear sanitary napkins Nos. (2-1)-(2-47), and the obtained responses indicated that with the sanitary napkins comprising blood modifying agents Nos. (2-1)-(2-32), the top sheets had no sticky feel and the top sheets were smooth, even after absorption of menstrual blood Also, with sanitary napkins Nos. (2-1)-(2-32), and particularly with sanitary napkins that comprised blood modifying agents Nos. (2-1)-(2-11), (2-15)-(2-19) and (2-32), the skin contact surfaces of the top sheets after absorption of menstrual blood had not been reddened by the blood and the unpleasantness was minimal.

Example 2

The rewetting rate was evaluated for blood from different animals in accordance with the above procedures. The following blood was used for the test.
[Animal Species]
 (1) Human
 (2) Horse
 (3) Sheep
[Types of Blood]
Defibrinated blood: blood sampled and agitated together with glass beads in an Erlenmeyer flask for approximately 5 minutes.
EDTA blood: 65 mL of venous blood with addition of 0.5 mL of a 12% EDTA·2K isotonic sodium chloride solution.
[Fractionation]
Serum or blood plasma: Supernatant obtained after centrifugation of defibrinated blood or EDTA blood for 10 minutes at room temperature at about 1900 G.

Blood cells: Obtained by removing the serum from the blood, washing twice with phosphate buffered saline (PBS), and adding phosphate buffered saline to the removed serum portion.

An absorbent article was produced in the same manner as Example 2, except that the tri-C2L oil fatty acid glyceride was coated at a basis weight of about 5 g/m$^2$, and the rewetting rate of each of the aforementioned blood samples was evaluated. Measurement was performed 3 times for each blood sample, and the average value was recorded.

The results are shown in Table 3 below.

TABLE 3

| | | | Rewetting rate (%) | |
|---|---|---|---|---|
| No. | Animal species | Type of blood | With blood modifying agent | Without blood modifying agent |
| 1 | Human | Defibrinated blood | 1.6 | 5.0 |
| 2 | | Defibrinated serum | 0.2 | 2.6 |
| 3 | | Defibrinated blood cells | 0.2 | 1.8 |
| 4 | | EDTA blood | 2.6 | 10.4 |
| 5 | | EDTA plasma | 0.0 | 5.8 |
| 6 | | EDTA blood cells | 0.2 | 4.3 |
| 7 | Horse | Defibrinated blood | 0.0 | 8.6 |
| 8 | | Defibrinated serum | 0.2 | 4.2 |
| 9 | | Defibrinated blood cells | 0.2 | 1.0 |
| 10 | | EDTA blood | 6.0 | 15.7 |
| 11 | | EDTA plasma | 0.1 | 9.0 |
| 12 | | EDTA blood cells | 0.1 | 1.8 |
| 13 | Sheep | Defibrinated blood | 0.2 | 5.4 |
| 14 | | Defibrinated serum | 0.3 | 1.2 |
| 15 | | Defibrinated blood cells | 0.1 | 1.1 |
| 16 | | EDTA blood | 2.9 | 8.9 |
| 17 | | EDTA plasma | 0.0 | 4.9 |
| 18 | | EDTA blood cells | 0.2 | 1.6 |

The same trend was seen with human and sheep blood as with the horse EDTA blood, as obtained in Example 2. A similar trend was also observed with defibrinated blood and EDTA blood.

Example 3

Evaluation of Blood Retention

The blood retention was evaluated for a top sheet comprising a blood modifying agent and a top sheet comprising no blood modifying agent.
[Test Methods]
 (1) A tri-C2L oil fatty acid glyceride was atomized on the skin contact surface of a top sheet formed from an air-through nonwoven fabric (composite fiber composed of polyester and polyethylene terephthalate, basis weight: 35 g/m$^2$), using a control seam HMA gun, for coating to a basis weight of about 5 g/m$^2$. For comparison, there was also prepared a sheet without coating with the tri-C2L oil fatty acid glyceride. Next, both the tri-C2L oil fatty acid glyceride-coated top sheet and the non-coated top sheet were cut to a size of 0.2 g, and the mass (a) of the cell strainer+top sheet was precisely measured.

(2) After adding about 2 mL of horse EDTA blood from the skin contact surface side, it was allowed to stand for 1 minute.

(3) The cell strainer was set in a centrifuge tube, and subjected to spin-down to remove the excess horse EDTA blood.

(4) The mass (b) of the top sheet containing the cell strainer+horse EDTA blood was measured.

(5) The initial absorption (g) per 1 g of top sheet was calculated by the following formula.

Initial absorption=[mass(b)−mass(a)]/0.2

(6) The cell strainer was again set in the centrifuge tube and centrifuged at room temperature for 1 minute at approximately 1,200 G.

(7) The mass (c) of the top sheet containing the cell strainer+horse EDTA blood was measured.

(8) The post-test absorption (g) per 1 g of top sheet was calculated by the following formula.

Post-test absorption=[mass(c)−mass(a)]/0.2

(9) The blood retention (%) was calculated according to the following formula.

Blood retention (%)=100×post-test absorption/initial absorption

The measurement was conducted 3 times, and the average value was recorded.

The results are shown in Table 4 below.

TABLE 4

| | Blood retention (%) | |
|---|---|---|
| | With blood modifying agent | Without blood modifying agent |
| Horse EDTA blood | 3.3 | 9.2 |

The top sheets comprising blood modifying agents had low blood retentions, suggesting that blood rapidly migrated into the absorbent body after absorption.

Example 4

Viscosity of Blood Containing Blood Modifying Agent

The viscosity of the blood modifying agent-containing blood was measured using a Rheometric Expansion System ARES (Rheometric Scientific, Inc.). After adding 2 mass % of PANACET 810s to horse defibrinated blood, the mixture was gently agitated to form a sample, the sample was placed on a 50 mm-diameter parallel plate, with a gap of 100 μm, and the viscosity was measured at 37±0.5° C. The sample was not subjected to a uniform shear rate due to the parallel plate, but the average shear rate indicated by the device was 10 s$^{-1}$.

The viscosity of the horse defibrinated blood containing 2 mass % PANACET 810s was 5.9 mPa·s, while the viscosity of the horse defibrinated blood containing no blood modifying agent was 50.4 mPa·s. Thus, the horse defibrinated blood containing 2 mass % PANACET 810s clearly had an approximately 90% lower viscosity than the blood containing no blood modifying agent.

It is known that blood contains components such as blood cells and has thixotropy, and it has been found that the blood modifying agent of this disclosure can lower blood viscosity in the low viscosity range. Lowering the blood viscosity presumably allows absorbed menstrual blood to rapidly migrate from the top sheet to the absorbent body.

Example 5

Photomicrograph of Blood Modifying Agent-Containing Blood

Menstrual blood was sampled from healthy volunteers onto Saran wrap, and PANACET 810s dispersed in a 10-fold mass of phosphate-buffered saline was added to a portion thereof to a PANACET 810s concentration of 1 mass %. The menstrual blood was dropped onto a slide glass, a cover glass was placed thereover, and the state of the erythrocytes was observed with an optical microscope. A photomicrograph of menstrual blood containing no blood modifying agent is shown in FIG. 7(a), and a photomicrograph of menstrual blood containing PANACET 810s is shown in FIG. 7(b).

Figure 7:
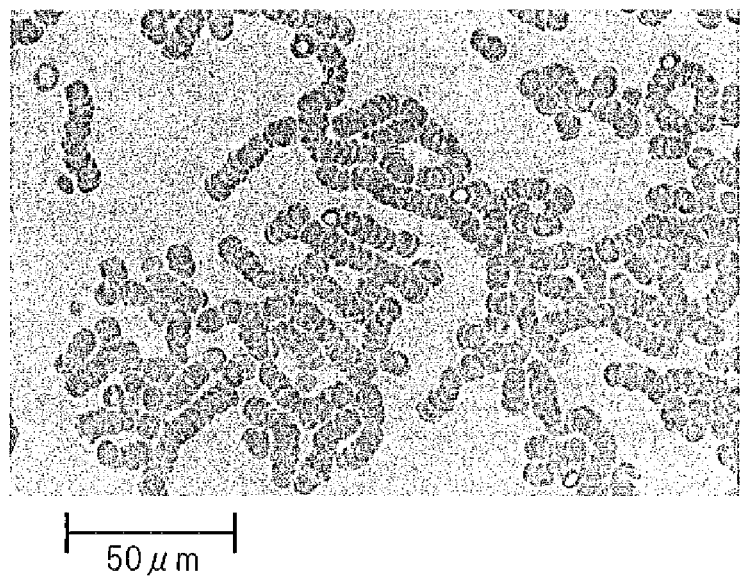
FIG. 7 is a pair of photomicrographs of menstrual blood containing and not containing a blood modifying agent.
Figure 7:
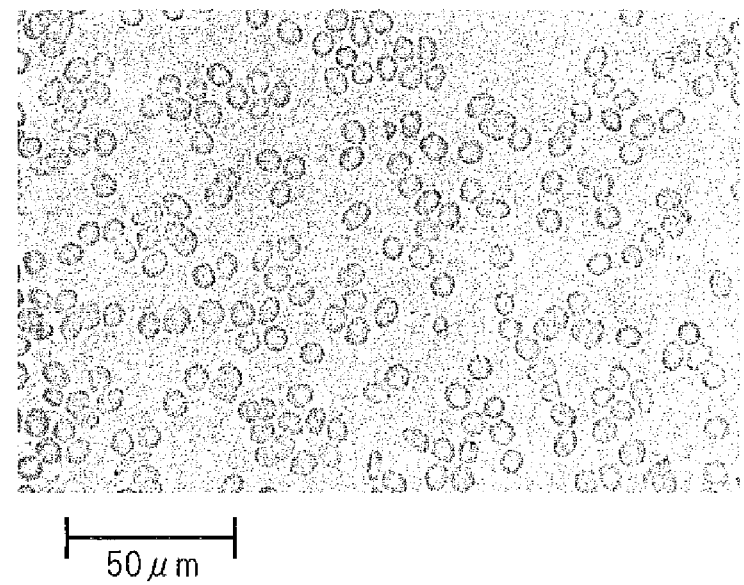

As shown FIG. 7, it is seen that the erythrocytes formed aggregates such as rouleaux in the menstrual blood containing no blood modifying agent, while the erythrocytes were stably dispersed in the menstrual blood containing PANACET 810s. This suggests that the blood modifying agent functions to stabilize erythrocytes in blood.

Example 6

Surface Tension of Blood Containing Blood Modifying Agent

The surface tension of blood containing a blood modifying agent was measured by the pendant drop method, using a Drop Master500 contact angle meter by Kyowa Interface Science Co., Ltd. The surface tension was measured after adding a prescribed amount of blood modifying agent to sheep defibrinated blood, and thoroughly shaking.

Figure 8:
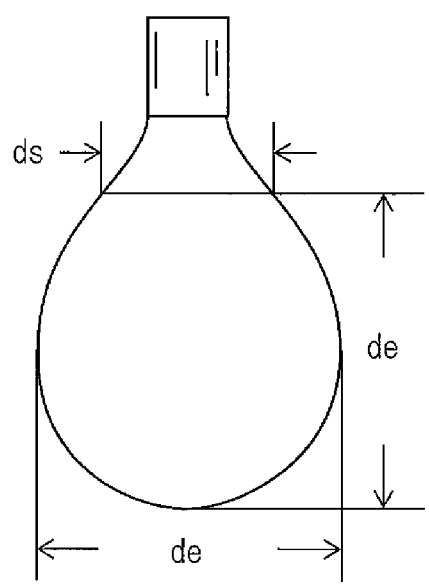
FIG. 8 is a diagram illustrating a method of measuring surface tension.

The measurement was accomplished automatically with a device, and the surface tension 7 was determined by the following formula (see FIG. 8).

$\gamma = g \times \rho \times (de)^2 \times 1/H$ g: Gravitational constant

1/H: Correction factor determined from ds/de

ρ: Density de: Maximum diameter ds: Diameter at location of increase by de from dropping edge The density ρ was measured at the temperatures listed in Table 5, according to JIS K 2249-1995, "Density test methods and density/mass/volume conversion tables", "5. Vibrating density test method".

The measurement was accomplished using a DA-505 by Kyoto Electronics Co., Ltd.

The results are shown in Table 5 below.

TABLE 5

| No. | Blood modifying agent Type | Amount (mass %) | Measuring temperature (° C.) | Surface tension (mN/m) |
|---|---|---|---|---|
| 1 | — | — | 35 | 62.1 |
| 2 | PANACET 810s | 0.01 | 35 | 61.5 |
| 3 |  | 0.05 | 35 | 58.2 |
| 4 |  | 0.10 | 35 | 51.2 |
| 5 | ELECTOL WE20 | 0.10 | 35 | 58.8 |
| 6 | PARLEAM 6 | 0.10 | 35 | 57.5 |
| 7 | — | — | 50 | 56.3 |
| 8 | WILBRITE cp9 | 0.10 | 50 | 49.1 |

Table 5 shows that the blood modifying agent can lower the surface tension of blood despite its very low solubility in water, as seen by a water solubility of about 0.00-about 0.05 g in 100 g of water at 25° C.

Lowering the surface tension of blood presumably allows absorbed blood to rapidly migrate from the top sheet to the absorbent body, without being retained between the top sheet fibers.

Example 7

Measurement of Opening Diameter of Openings in Absorbent Article (Measuring Method)

An X-ray CT apparatus was used to photograph a sectional image of an absorbent article (sanitary napkin). A stereoscopic image was created from the sectional image using analysis software. A cross-sectional image of an opening formed in the absorbent article was constructed from the stereoscopic image, and the opening diameter was measured.

(Apparatuses Used)

Three-dimensional X-ray CT apparatus (TDM1000-IS/SP, product of Yamato Scientific Co., Ltd.)

Three-dimensional volume rendering software (VG-Studio MAX, product of Nihon Visual Science, Inc.

(Measuring Conditions)

Tube voltage: 40 kV

Tube current: 20 μA

Resolution: 1024×1024 pixel

Visual field size: 12.0 mm$\phi$×12.mmh (Results)

Figure 9:
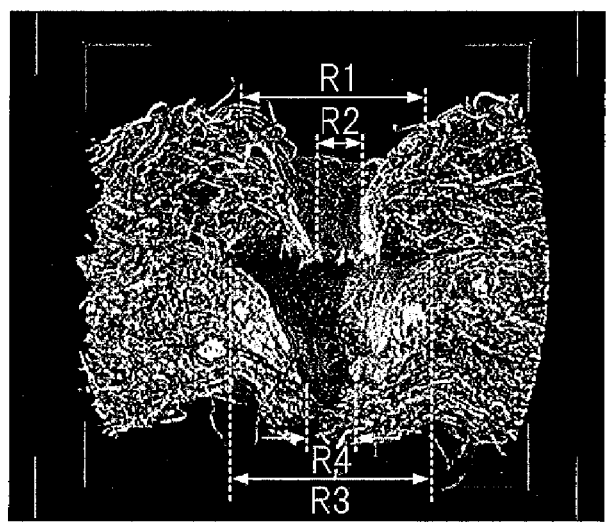
FIG. 9 is a cross-sectional view of an opening formed in an absorbent article.
Figure 9:
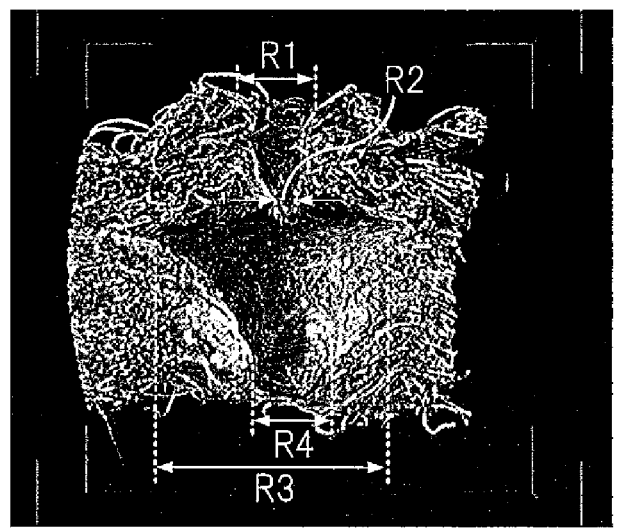

Sectional images for openings at two locations (opening A and B), among the openings formed in the absorbent article, are shown in FIG. 9. FIG. 9(a) is a sectional image of opening A, and FIG. 9(b) is a sectional image of opening B. Table 6 shows the opening diameters measured from the sectional images.

TABLE 6

Measurement results for opening diameter of openings formed in absorbent articles

| Opening | Opening diameter R1 | Opening diameter R2 | Opening diameter R3 | Opening diameter R4 |
|---|---|---|---|---|
| Opening A | 2.38 mm | 0.81 mm | 2.69 mm | 0.68 mm |
| Opening B | 0.59 mm | 0.23 mm | 2.86 mm | 0.92 mm |

Explanation of Symbols 1, 1A Absorbent articles
2 Top sheet
3 Back sheet
4 Absorbent body
5 Side sheet
6 Body section
7 Wing section
8 Blood modifying agent-coated region
9 Second sheet
10 Opening
11 Compressed groove
12, 13 Seal sections
14, 15 Pressure-sensitive adhesive sections
112 Top sheet
114 Absorbent body
120 Through-hole forming apparatus
130 Embossing apparatus

What is claimed is:

1. An absorbent article, comprising:
a liquid-permeable top sheet provided on a skin side and having openings running through in a thickness direction,
a liquid-impermeable back sheet provided on a clothing side, and
a liquid-retaining absorbent body situated between the top sheet and the back sheet and having openings that are provided at locations in the thickness direction corresponding to the openings of the top sheet and that run through the thickness direction,
wherein
the top sheet is detached from the absorbent body at the openings of the top sheet and the openings of the absorbent body,
opening diameters of the openings on the clothing side of the top sheet are smaller than opening diameters of the openings on the skin side of the absorbent body, and
opening diameters of the openings on the clothing side of the absorbent body are not greater than the opening diameters of the openings on the clothing side of the top sheet.

2. The absorbent article according to claim 1, wherein opening diameters of the openings on the skin side of the top sheet are smaller than the opening diameters of the openings on the skin side of the absorbent body.

3. The absorbent article according to claim 1, further comprising a wrap sheet covering an outer side of the absorbent body and covering interiors of the openings of the absorbent body.

4. The absorbent article according to claim 1, wherein the top sheet has a blood modifying agent-coated region in which a blood modifying agent is coated at least on regions in which the openings are formed, the blood modifying agent having an IOB of 0.00-0.60, a melting point of no higher than 45° C. and a water solubility of 0.00 to 0.05 g in 100 g of water at 25° C.

5. The absorbent article according to claim 4, wherein the blood modifying agent is selected from the group consisting of the following items (i)-(iii), and any combination thereof:
(i) a hydrocarbon;
(ii) a compound having (ii-1) a hydrocarbon moiety, and (ii-2) one or more groups each selected from the group consisting of carbonyl group (—CO—) and oxy group (—O—) inserted between a C—C single bond of the hydrocarbon moiety; and
(iii) a compound having (iii-1) a hydrocarbon moiety, (iii-2) one or more groups each selected from the group consisting of carbonyl group (—CO—) and oxy group (—O—) inserted between a C—C single bond of the hydrocarbon moiety, and (iii-3) one or more groups each selected from the group consisting of carboxyl group (—COOH) and hydroxyl group (—OH) substituting a hydrogen of the hydrocarbon moiety;

wherein when 2 or more oxy groups are inserted in the compound of (ii) or (iii), the oxy groups are not adjacent.

6. The absorbent article according to claim 4, wherein the blood modifying agent is selected from the group consisting of the following items (i')-(iii'), and any combination thereof:
(i') a hydrocarbon;
(ii') a compound having at least (ii'-1) a hydrocarbon moiety, and (ii'-2) one or more bonds each selected from the group consisting of carbonyl bond (—CO—), at least one ester bond (—COO—), at least one carbonate bond (—OCOO—), and at least one ether bond (—O—) inserted between a C—C single bond of the hydrocarbon moiety; and
(iii') a compound having at least (iii'-1) a hydrocarbon moiety, (iii'-2) one or more bonds each selected from the group consisting of carbonyl bond (—CO—), at least one ester bond (—COO—), at least one carbonate bond (—OCOO—), and at least one ether bond (—O—) inserted between a C—C single bond of a hydrocarbon moiety, and (iii'-3) one or more groups each selected from the group consisting of carboxyl group (—COOH) and hydroxyl group (—OH) substituting a hydrogen on the hydrocarbon moiety;

wherein when 2 or more same or different bonds are inserted in the compound of (ii') or (iii'), the bonds are not adjacent.

7. The absorbent article according to claim 4, wherein the blood modifying agent is selected from the group consisting of the following items (A)-(F), and any combination thereof:
(A) an ester of (A1) a compound having a chain hydrocarbon moiety and 2-4 hydroxyl groups substituting hydrogens on the chain hydrocarbon moiety, and (A2) a compound having a chain hydrocarbon moiety and 1 carboxyl group substituting a hydrogen on the chain hydrocarbon moiety;
(B) an ether of (B1) a compound having a chain hydrocarbon moiety and 2-4 hydroxyl groups substituting hydrogens on the chain hydrocarbon moiety and (B2) a compound having a chain hydrocarbon moiety and 1 hydroxyl group substituting a hydrogen on the chain hydrocarbon moiety;
(C) an ester of (C1) a carboxylic acid, hydroxy acid, alkoxy acid or oxoacid comprising a chain hydrocarbon moiety and 2-4 carboxyl groups substituting hydrogens on the chain hydrocarbon moiety and (C2) a compound having a chain hydrocarbon moiety and 1 hydroxyl group substituting a hydrogen on the chain hydrocarbon moiety;
(D) a compound having a chain hydrocarbon moiety and one bond selected from the group consisting of an ether bond (—O—), carbonyl bond (—CO—), ester bond (—COO—) and carbonate bond (—OCOO—) inserted between a C—C single bond of the chain hydrocarbon moiety;
(E) a polyoxy $C_2$-$C_6$ alkylene glycol, or alkyl ester or alkyl ether thereof; and
(F) a chain hydrocarbon.

8. The absorbent article according to claim 4, wherein the blood modifying agent is selected from the group consisting of ($a_1$) esters of chain hydrocarbon tetraols and at least one fatty acid, ($a_2$) esters of chain hydrocarbon triols and at least one fatty acid, ($a_3$) esters of chain hydrocarbon diols and at least one fatty acid, ($b_1$) ethers of chain hydrocarbon tetraols and at least one aliphatic monohydric alcohol, ($b_2$) ethers of chain hydrocarbon triols and at least one aliphatic monohydric alcohol, ($b_3$) ethers of chain hydrocarbon diols and at least one aliphatic monohydric alcohol, ($c_1$) esters of chain hydrocarbon tetracarboxylic acids, hydroxy acids, alkoxy acids or oxoacids with 4 carboxyl groups, and at least one aliphatic monohydric alcohol, ($c_2$) esters of chain hydrocarbon tricarboxylic acids, hydroxy acids, alkoxy acids or oxoacids with 3 carboxyl groups, and at least one aliphatic monohydric alcohol, ($c_3$) esters of chain hydrocarbon dicarboxylic acids, hydroxy acids, alkoxy acids or oxoacids with 2 carboxyl groups, and at least one aliphatic monohydric alcohol, ($d_1$) ethers of aliphatic monohydric alcohols and aliphatic monohydric alcohols, ($d_2$) dialkyl ketones, ($d_3$) esters of fatty acids and aliphatic monohydric alcohols, ($d_4$) dialkyl carbonates, ($e_1$) polyoxy $C_2$-$C_6$ alkylene glycols, ($e_2$) esters of polyoxy $C_2$-$C_6$ alkylene glycols and at least one fatty acid, ($e_3$) ethers of polyoxy $C_2$-$C_6$ alkylene glycols and at least one aliphatic monohydric alcohol, ($e_4$) esters of polyoxy $C_2$-$C_6$ alkylene glycols with chain hydrocarbon tetracarboxylic acids, chain hydrocarbon tricarboxylic acids or chain hydrocarbon dicarboxylic acids, ($e_5$) ethers of polyoxy $C_2$-$C_6$ alkylene glycols with chain hydrocarbon tetraols, chain hydrocarbon triols or chain hydrocarbon diols, and ($f_1$) chain alkanes.

9. An absorbent article, comprising;
a liquid-permeable top sheet provided on a skin side and having openings running through in a thickness direction,
a liquid-impermeable back sheet provided on a clothing side,
a liquid-retaining absorbent body situated between the top sheet and the back sheet and having openings that are provided at locations in the thickness direction corresponding to the openings of the top sheet and that run through the thickness direction, and
a liquid-permeable second sheet provided between the top sheet and the absorbent body, and having openings that are provided at locations in the thickness direction corresponding to the openings of the top sheet and that run through the thickness direction, wherein:
the second sheet is detached from the absorbent body at the openings of the second sheet and the openings of the absorbent body,
opening diameters of the openings on the clothing side of the second sheet are smaller than opening diameters of the openings on the skin side of the absorbent body, and
opening diameters of the openings on the clothing side of the absorbent body are not greater than the opening diameters of the openings on the clothing side of the second sheet.

10. The absorbent article according to claim 9, wherein opening diameters of the openings on the skin side of the top sheet are smaller than the opening diameters of the openings on the skin side of the absorbent body.

11. An absorbent article, comprising:
a liquid-permeable top sheet provided on a skin side and having openings running through in a thickness direction,
a liquid-impermeable back sheet provided on a clothing side, and
a liquid-retaining absorbent body situated between the top sheet and the back sheet and having openings that are provided at locations in the thickness direction corresponding to the openings of the top sheet and that run through the thickness direction, or else extend in but do not run through the thickness direction, wherein the top sheet is detached from the absorbent body at the openings of the top sheet and the openings of the absorbent body, opening diameters of the openings on the clothing side of the top sheet are smaller than opening diameters of the openings on the skin side of the absorbent body, and the top sheet has a blood modifying agent-coated region in which a blood modifying agent is coated at least on regions in which the openings are formed, the blood modifying agent having an IOB of 0.00-0.60, a melting point of no higher than 45° C. and a water solubility of 0.00 to 0.05 g in 100 g of water at 25° C.

* * * * *